US011690437B2

(12) United States Patent
Bartlett et al.

(10) Patent No.: US 11,690,437 B2
(45) Date of Patent: Jul. 4, 2023

(54) MEDICAL BACKPACK

(71) Applicant: Auburn University, Auburn, AL (US)

(72) Inventors: Randall N. Bartlett, Auburn, AL (US); Scott W. Kramer, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 17/674,443

(22) Filed: Feb. 17, 2022

(65) Prior Publication Data
US 2022/0257000 A1 Aug. 18, 2022

Related U.S. Application Data

(60) Provisional application No. 63/150,215, filed on Feb. 17, 2021.

(51) Int. Cl.
*A45F 3/04* (2006.01)
*A61B 50/30* (2016.01)
*A45F 3/00* (2006.01)

(52) U.S. Cl.
CPC .............. *A45F 3/04* (2013.01); *A61B 50/30* (2016.02); *A45F 2003/003* (2013.01); *A45F 2003/045* (2013.01); *A61B 2050/301* (2016.02); *A61B 2050/3008* (2016.02); *A61B 2050/318* (2016.02)

(58) Field of Classification Search
CPC ........ A45F 4/06; A45F 4/08; A61B 2050/301; A45C 13/02
USPC ........ 224/156, 576, 577, 153, 158, 651, 250
See application file for complete search history.

(56) References Cited

U.S. PATENT DOCUMENTS

| 4,609,084 A | * | 9/1986 | Thomas | A61F 17/00 190/110 |
| 5,649,658 A | * | 7/1997 | Hoffman | A47D 5/006 5/655 |
| 5,845,780 A | * | 12/1998 | Allen | A45C 3/00 190/110 |
| 6,193,118 B1 | * | 2/2001 | Kearl | A45C 7/0095 224/655 |
| 6,742,635 B2 | * | 6/2004 | Hirshberg | A45C 9/00 224/576 |
| 7,600,619 B2 | | 10/2009 | Sapyta | |

(Continued)

FOREIGN PATENT DOCUMENTS

| DE | 202006020143 | 1/2008 | |
| EP | 1321065 A1 * | 6/2003 | ............... A45C 3/10 |

(Continued)

OTHER PUBLICATIONS

International Search Report and Written Opinion dated May 11, 2022 of corresponding International Patent Application No. PCT/US2022/016789.

Primary Examiner — Scott T McNurlen
(74) Attorney, Agent, or Firm — Bradley Arant Boult Cummings LLP

(57) ABSTRACT

A medical backpack for storing medical supplies and medical equipment is disclosed. The medical backpack can be used by medics working in rural or remote areas that are not accessible by car and where access to hospitals and medical supplies is limited or non-existent. The medical backpack is light enough to carry long distances and comprised of a number of different compartments that are flexible to equip with various supplies for specific needs and circumstances.

14 Claims, 14 Drawing Sheets

(56) References Cited

U.S. PATENT DOCUMENTS

| | | | |
|---|---|---|---|
| 7,856,689 B2* | 12/2010 | Habimana | A47D 5/00 |
| | | | 5/655 |
| 9,101,190 B2* | 8/2015 | Noble | A45C 13/28 |
| 10,251,464 B2 | 4/2019 | Seuk | |
| 2002/0074251 A1 | 6/2002 | Hirshberg | |
| 2002/0166881 A1* | 11/2002 | Willingham | A45C 7/0095 |
| | | | 224/582 |
| 2004/0094583 A1* | 5/2004 | Bernbaum | A45F 3/047 |
| | | | 224/153 |
| 2007/0000089 A1 | 1/2007 | Morales | |
| 2007/0272719 A1* | 11/2007 | Laughton | A45F 3/04 |
| | | | 224/629 |
| 2009/0052809 A1 | 2/2009 | Sampson | |
| 2011/0204114 A1* | 8/2011 | Miller | A45F 3/06 |
| | | | 224/582 |
| 2012/0018477 A1 | 1/2012 | Inouye | |
| 2013/0228408 A1 | 9/2013 | Lease et al. | |
| 2013/0228600 A1 | 9/2013 | Teixeira | |
| 2014/0090175 A1* | 4/2014 | Thrailkill | A47D 5/006 |
| | | | 5/655 |
| 2015/0041511 A1 | 2/2015 | Powell | |
| 2020/0037719 A1* | 2/2020 | Jaworski | A45C 5/02 |

FOREIGN PATENT DOCUMENTS

| | | |
|---|---|---|
| FR | 2 814 940 | 3/2003 |
| JP | 4937433 | 5/2012 |

* cited by examiner

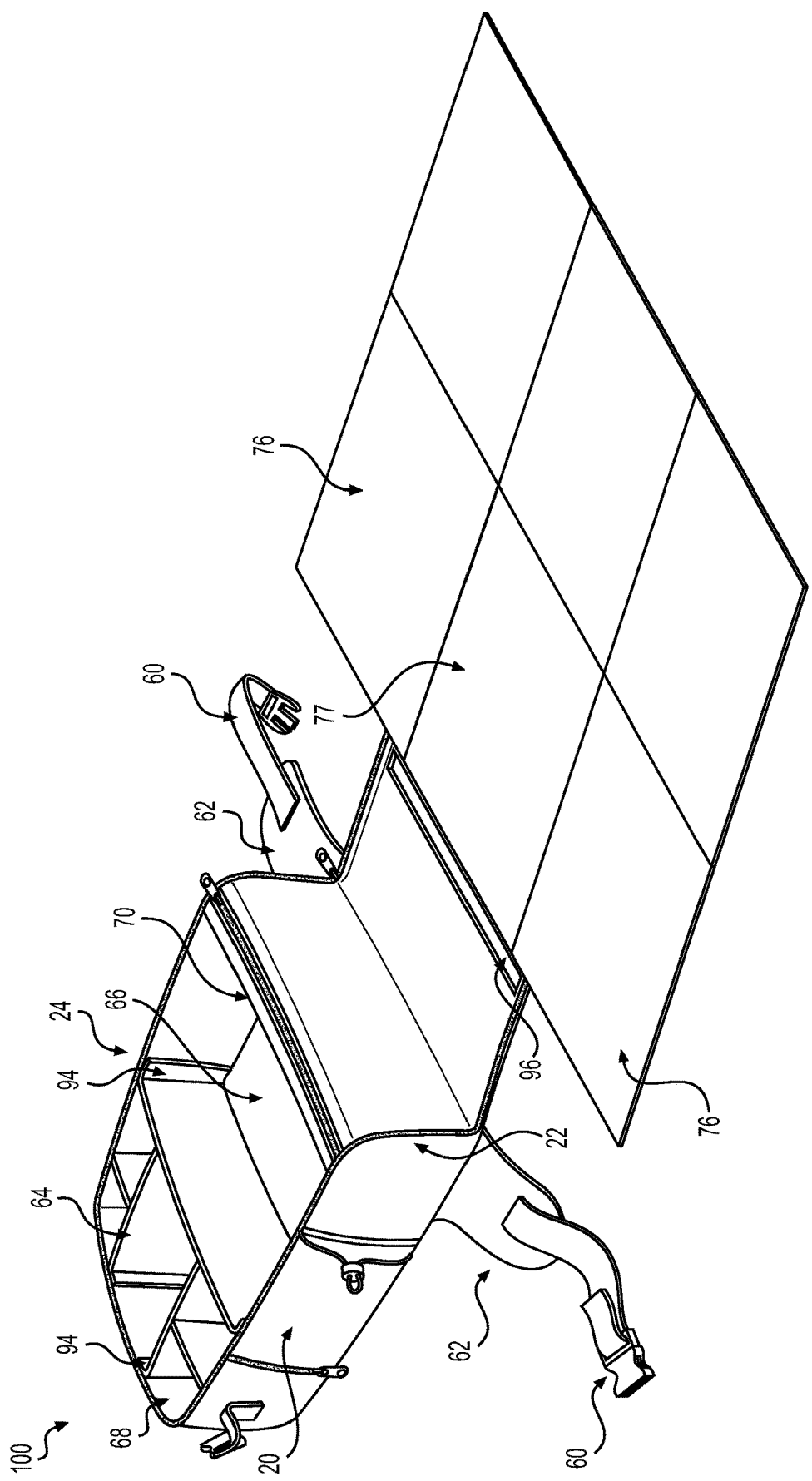

MEDICAL BACKPACK

CROSS-REFERENCE TO RELATED APPLICATIONS

This application claims the benefit of and priority to U.S. Provisional Application No. 63/150,215, filed on Feb. 17, 2021, and entitled "AU MEDICAL BACKPACK," the disclosure of which is expressly incorporated by reference in its entirety.

TECHNICAL FIELD

The present invention relates generally to backpacks, and more particularly, to a backpack that is intended to hold supplies that a medic may need to diagnose and treat a number of minor and more life-threatening illnesses in remote locations.

BACKGROUND

Medical missionaries and global healthcare professionals travel to very remote areas throughout the world to respond to natural disasters, deliver medical services, and improve the health of those living in poverty or near-poverty conditions. These medical professionals face many challenges as they try to provide healthcare to those in mountainous or other rural areas. The locations that the medical professionals must reach are often only accessible by walking trails and are hundreds of miles away from hospitals and doctors' offices. Hence, these medical professionals must carry all of the medical supplies and equipment that they may need to treat patients in these remote locations. While a variety of medical backpacks currently exist on the market, these backpacks are bulky and heavy and must often be carried by hand. Accordingly, there remains a need in the art for an improved medical bag that is light enough to carry long distances and through treacherous terrain but that can also hold everything a healthcare provider may need to treat patients for a variety of needs from minor injuries to life-threatening illnesses.

SUMMARY

The problems expounded above, as well as others, are addressed by the following inventions, although it is to be understood that not every embodiment of the inventions described herein will address each of the problems described above. The present disclosure describes different embodiments of certain medical backpacks.

In some embodiments, a medical backpack is provided, the medical backpack including a backpack body defining an interior cavity, the backpack body defined by a front surface having four edges, a rear surface, a top surface, a bottom surface, and opposing lateral surfaces, a zipper fastener extending along three of the four edges defining the front surface, wherein the zipper fastener unzips to enable the front surface to rotate outwardly with respect to the remaining portions of the backpack body, and thereby enabling access to the interior cavity, an expandable mesh pocket positioned on the backpack body, wherein the expandable mesh pocket comprises an adjustable cord, at least one shoulder strap coupled to the backpack body, a plurality of dividers arranged within the interior cavity to form a main compartment and a plurality of ancillary compartments, wherein the main compartment is configured for receiving a plurality of internal bags, wherein each internal bag is configured for storing a specific medical supply or device.

The backpack body may include a plurality of attachment points configured for attaching hooks or carabiners thereto. In other embodiments, the medical backpack may include a handle enclosed within a curved, tubular metal cover. In still other embodiments, the medical backpack may include a zippered pocket positioned above an expandable mesh pocket on the backpack body. In yet other embodiments, the medical backpack may include a pocket positioned within and below the main compartment of the interior cavity and configured for storing a portable stretcher. In further embodiments, the interior cavity may include a plurality of securing straps for securing the internal bags within the main compartment. In still further embodiments, each of the ancillary compartments has a volume that is less than the volume of the main compartment.

In other embodiments, a medical backpack is provided, the medical backpack including a backpack body defining an interior cavity, the backpack body defined by a front surface having four edges, a rear surface, a top surface, a bottom surface, and opposing lateral surfaces, a zipper fastener extending along three of the four edges defining the front surface, wherein the zipper fastener unzips to enable the front surface to rotate outwardly with respect to the remaining portions of the backpack body so that the front surface lies substantially coplanar with the rear surface, an anchoring panel affixed to an inner portion of the front surface, and a folding panel operatively connected to the anchoring panel and configured to fold outwardly from the anchoring panel to create a substantially flat work surface.

The anchoring panel and the folding panel may be formed of a material selected from the group consisting of acrylonitrile butadiene styrene (ABS), acetal, acrylic, polyvinyl chloride (PVC), polyester, high-density polyethylene (HDPE), polystyrene, nylon, polycarbonate, polypropylene, and any combination thereof. For example, the anchoring panel and the folding panel may be formed of a first layer comprising ABS and a second layer comprising polyester. In some embodiments, the medical backpack further includes a plurality of dividers arranged within the interior cavity to form a main compartment and a plurality of ancillary compartments, and a plurality of internal bags secured within the main compartment. In other embodiments, the plurality of internal bags includes a first internal bag having a first length and a second internal bag having a second length, wherein the second length is longer than the first length. In still other embodiments, each of the internal bags includes a fastener configured for securing the internal bags to one another. In yet other embodiments, each internal bag is directed to a specific medical supply or device and includes a label affixed thereto identifying the specific medical supply or device stored therein.

In still other embodiments, a medical backpack is provided, the medical backpack including a backpack body defining an interior cavity, the backpack body further including a front surface, a pocket within the interior cavity configured for storing a portable stretcher, the portable stretcher having a proximal end and a distal end, wherein the proximal end is attached to the backpack body, the front surface further including a slot in alignment with the pocket, wherein the portable stretcher is configured to extend through the slot such that the distal end of the portable stretcher is external to the backpack body and the proximal end remains attached to the backpack body.

The medical backpack may further include a strapping system including two shoulder straps coupled to the backpack body, a chest strap coupled to the two shoulder straps, and an adjustable waistband coupled to the backpack body. In other embodiments, the medical backpack may further include a plurality of dividers arranged within the interior cavity to form a main compartment and a plurality of ancillary compartments, and a plurality of internal bags secured within the main compartment. The plurality of internal bags may include a first internal bag configured for storing a suture kit, a second internal bag configured for storing a wound care kit, a third internal bag configured for storing medication, a fourth internal bag configured for storing a baby delivery kit, a fifth internal bag configured for storing a stethoscope, blood pressure equipment, or a combination thereof, and a sixth internal bag configured for storing an otoscope. In other embodiments, each of the internal bags includes a label removably attached thereto identifying a medical supply or device stored therein. In still other embodiments, each of the internal bags includes a fastener configured for securing the internal bags to one another.

BRIEF DESCRIPTION OF THE DRAWINGS

Further features and advantages can be ascertained from the following detailed description that is provided in connection with the drawings described below:

FIG. 8A is a perspective view of the interior of the medical backpack with a plurality of panels folded outwardly according to one embodiment of the present disclosure.

DETAILED DESCRIPTION

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Numerical quantities given in this description are approximate unless stated otherwise, meaning that the term "about" or "approximately" can be inferred when not expressly stated.

The terminology used herein is for the purpose of describing particular embodiments only and is not intended to be limiting. As used herein, the singular forms "a", "an" and "the" are intended to include the plural (i.e., "at least one") forms as well, unless the context clearly indicates otherwise.

The terms "first," "second," "third," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Spatially relative terms, such as "above," "under," "below," "lower," "over," "upper," and the like, may be used herein for ease of description to describe one element or feature's relationship to another.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

Figure 1:
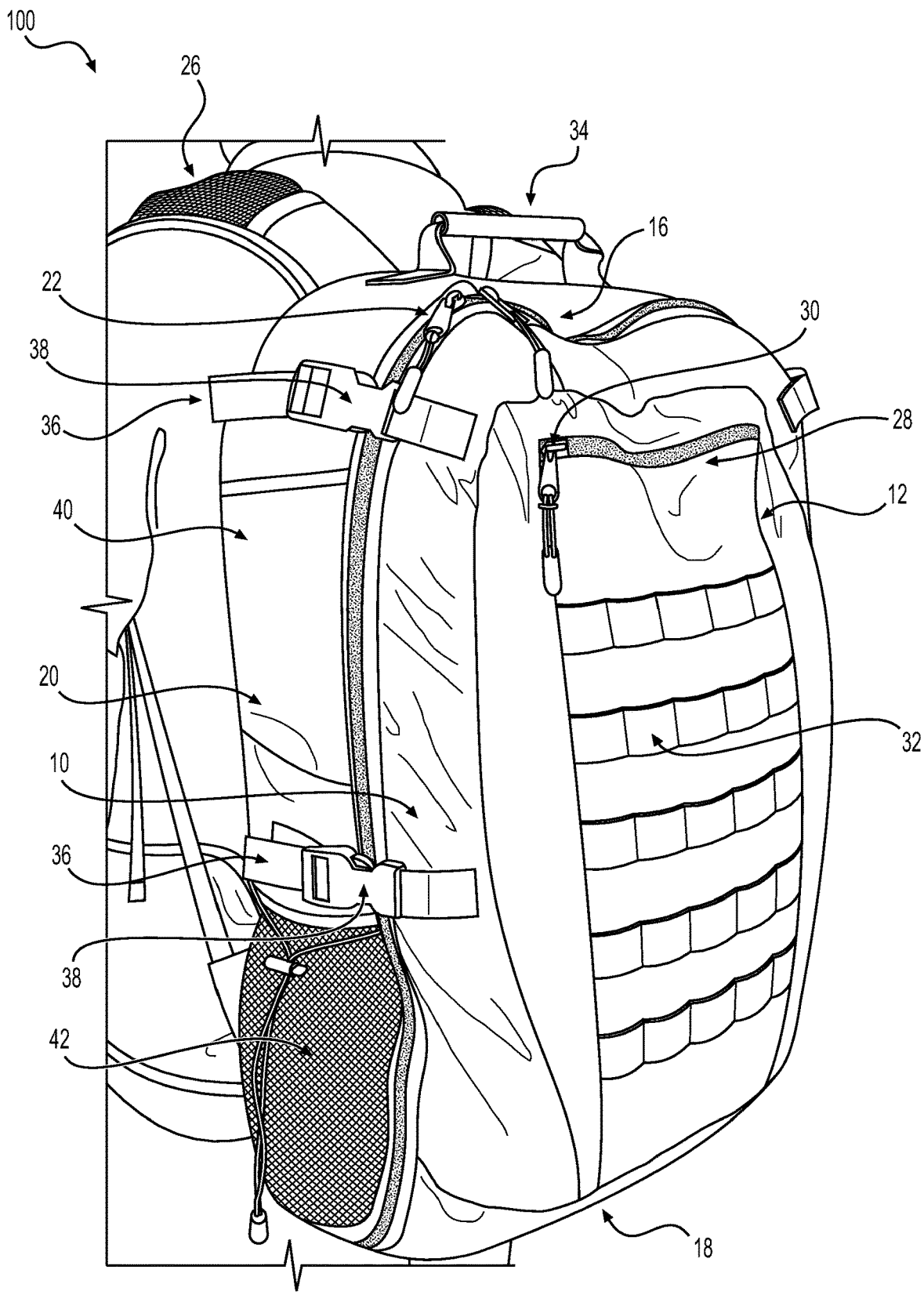
FIG. 1 is a front perspective view of the exterior of a medical backpack according to an exemplary embodiment of the present disclosure.

Referring to FIG. 1, a medical backpack 100 according to an exemplary embodiment of the present disclosure is shown. The medical backpack 100 is configured to store supplies that a medic may need to diagnose and treat patients for a variety of needs from minor injuries to life-threatening illnesses. The medical backpack 100 is particularly advantageous for medics working in rural or remote areas that are not accessible by car and where access to hospitals and medical supplies is limited or non-existent. The medical backpack 100 is light enough to carry long distances and comprised of a number of different compartments that are modular and flexible to equip for specific needs and circumstances.

The medical backpack 100 includes a body 10 constructed of a flexible, durable material. Suitable materials include, but are not limited to, canvas, cotton, nylon, fabric, or other flexible and durable materials. The material may be treated or otherwise constructed to provide durability, wear resistance, weather proofing, and/or waterproofing. Although the body 10 may be constructed primarily of a flexible material, it is to be appreciated that some portions of the body 10 may be stiffened to provide a certain amount of rigidity and shape retention.

As illustrated in FIG. 1, the body 10 includes a front surface 12, a rear surface (not shown), a top surface 16, a bottom surface 18, and opposing lateral surfaces 20. The front surface 12 faces away from a user carrying the medical backpack, while the rear surface faces the user's back portion. The opposing lateral surfaces 20 extend between the front surface 12 and the rear surface. The body 10 defines an interior cavity (not shown) that can be used to store various medical equipment and supplies. A main zipper 22 extends along three of the four edges defining the front surface 12, and unzips to enable the front surface 12 to rotate outwardly, thereby enabling access to the interior cavity. FIG. 1 illustrates the medical backpack 100 with the main zipper 22 in a fully closed configuration. In this configuration, the medical supplies and equipment stored within the interior cavity are secured. As illustrated, the main zipper 22 extends in a substantially U-shaped configuration, with the U-shape being inverted so as to be upside down.

In some embodiments, each of the opposing lateral surfaces 20 may include one or more straps 36 that extend from the front surface 12 to the rear surface. As shown in FIG. 1, the straps 36 are releasably secured with a buckle 38, though other releasable securing mechanisms may also be used with the straps 36, such as clasps, snap-hooks, and snap release buckles. In the illustrated embodiment, the opposing lateral surfaces 20 each include two straps 36 extending from the front surface 12 to the rear surface. The straps 26 may be used to reinforce the main zipper 22 and to keep the medical supplies and equipment secured within the interior cavity. As will be described in more detail below, each of the opposing lateral surfaces 20 may also include various external pockets, such as an upper external pocket 40 and a lower external pocket 42.

In further embodiments, the front surface 12 may include an outer pocket 28 that is accessible from outside the medical backpack 100. The outer pocket 28 has a lateral zipper 30 that may be used to open and close the outer pocket 28. The main zipper 22 and the lateral zipper 30 may utilize heavy duty zipper pulls with cords for easy access. The front surface 12 may further include a plurality of attachment points 32 configured for attaching hooks or carabiners thereto. In the illustrated embodiment, the attachment points 32 are loops. Hooks or carabiners having medical or other supplies attached thereto may snap onto the attachment points 32 and hang from the front surface 12 so that they are easily accessible to the user. For example, a user may desire to hang regularly used items, such as sanitizer or medical waste bags, from the attachment points 32. In some embodiments, a user may hang one or more solar panels from the attachment points 32. The solar panels may be rolled up and hung from the attachment points 32 for easy access. The solar panels can be used for generation of power that may be supplied to the user. For example, the solar panels can be used to recharge electronic devices and used as a power source for diagnostic testing. Each solar panel may include at least one solar cell that is comprised of a plurality of photovoltaic cells. In further embodiments, the solar panels may be rolled up and stored in the outer pocket 28. In still further embodiments, the front surface 12 may include additional outer pockets for storage of additional solar panels.

The medical backpack 100 may include a number of different mechanisms for carrying the backpack 100. As illustrated in FIG. 1, a handle 34 may protrude from the top surface 16 allowing a user to carry the medical backpack 100 by hand. In further embodiments, the rear surface 14 may have two shoulder straps 26 coupled thereto. The shoulder straps 26 can allow for the user to carry the medical backpack 100 on the user's back. In the illustrated embodiment, the medical backpack 100 includes two shoulder straps 26, though any number of shoulder straps 26 (for example, one or more) may be provided. As will be described in more detail below, the shoulder straps 26 may include various structural attributes such as having adjustability structures, accessory clips, padding, and the like.

Figure 2A:
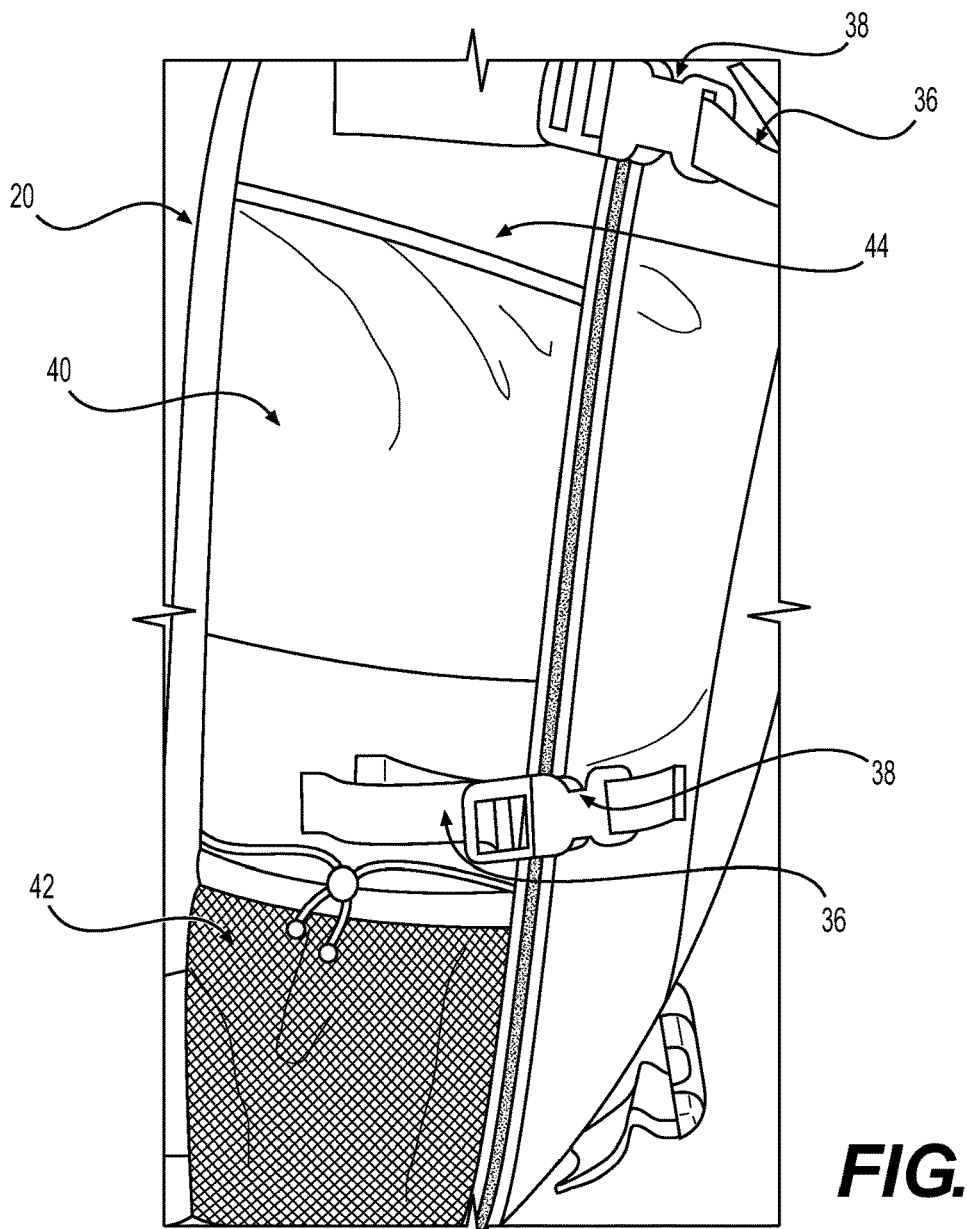
FIG. 2A is a side view of the exterior of the medical backpack according to one embodiment of the present disclosure.
Figure 2B:
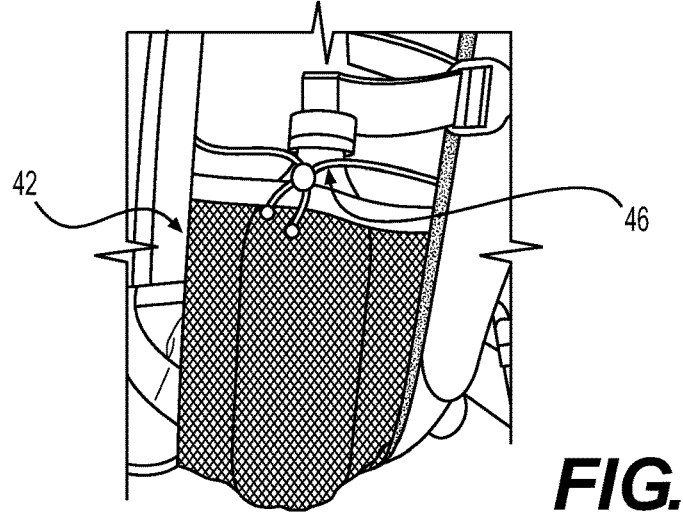
FIG. 2B is a side view of a lower pocket on the exterior of the medical backpack according to one embodiment of the present disclosure.

FIGS. 2A and 2B show a lateral surface 20 of the body 10 having the upper external pocket 40 and the lower external pocket 42. The upper external pocket 40 may include a zipper 44 that extends horizontally across the upper portion of the pocket 40. The zipper 44 enables the upper external pocket 40 to be fully enclosed to prevent items stored therein from falling out. Though the upper external pocket 40 is illustrated with a zipper, other enclosure mechanisms may be utilized to close the external pocket 40, such as a snap fastener. In the illustrated embodiment, the upper external pocket 40 has a width that is sized to extend from the front surface 12 to the rear surface 14 and a length that is sized to extend along at least a portion of the length of the lateral surface 20. However, as will be apparent to those skilled in the art, the upper external pocket 40 may have different sizing depending on the items desired to be stored therein.

The lower external pocket 42 is an expansion pocket that is affixed or stitched to the lateral surface 20. In an exemplary embodiment, the lower external pocket 42 is made of a mesh panel that is flexible and expandable. In the embodiment illustrated in FIG. 2B, the lower external pocket 42 includes an adjustable cord 46 provided along an upper portion of the lower external pocket 42. For example, the adjustable cord 46 may include a drawstring feature. The adjustable cord 46 (and the mesh panel) limits the amount of opening or expansion of the lower external pocket 42. The lower external pocket 42 may be designed to hold, for example, a water bottle, cell phone, or other item, by placing the item within the lower external pocket 42 and tightening the adjustable cord 46 against the item stored therein. In other embodiments, the lower external pocket 42 may be designed to hold a sharps container that enables used sharp objects, such as used needles, to be inserted therein for proper disposal later.

The illustrated embodiment shown in FIGS. 2A and 2B shows the upper external pocket 40 and the lower external pocket 42 on one lateral surface 20. However, those of ordinary skill in the art will appreciate that the opposing lateral surface 20 may also include an upper external pocket and a lower external pocket. In other embodiments, each lateral surface 20 may include only the upper external pocket 40 or only the lower external pocket 42 depending on the items the user desires to store in the pockets. In addition, if the medical backpack 100 includes one or more straps 36, the straps 36 should be positioned such that the straps 36 do not interfere with the enclosure mechanisms used on the upper external pocket 40 and the lower external pocket 42, such as the zipper 44 and the adjustable cord 46, respectively.

Figure 3:
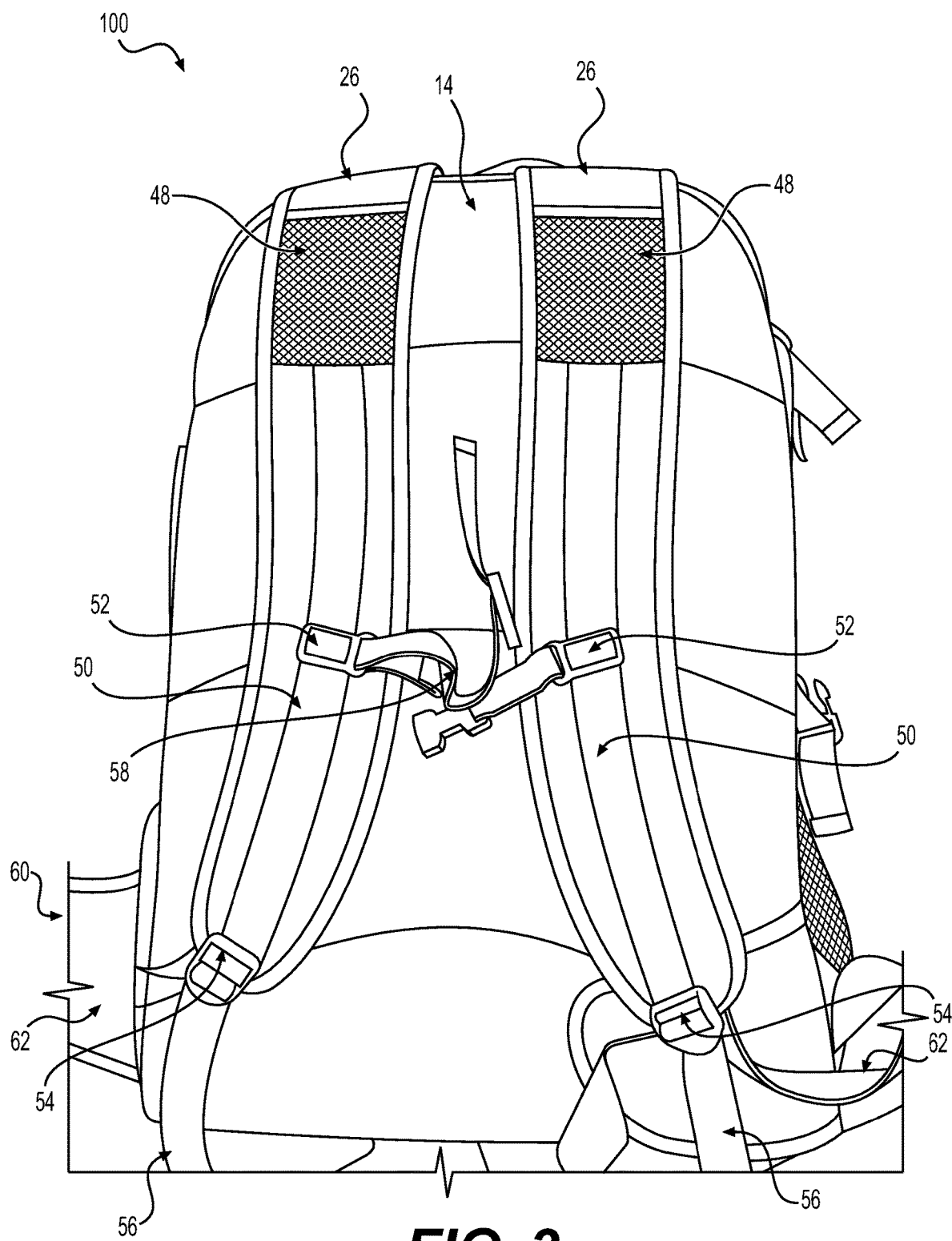
FIG. 3 is a rear view of the exterior of the medical backpack according to an exemplary embodiment of the present disclosure.

FIG. 3 shows a rear surface 14 of the body 10 according to an exemplary embodiment of the present disclosure. As shown in FIG. 3, the rear surface 14 has two shoulder straps 26 affixed to it. Each shoulder strap 26 may include a pocket 48 positioned at an upper end. In the illustrated embodiment, the pocket 48 is composed of a mesh panel. Each pocket 48 has an opening along the upper edge. The pockets 48 may be sized and dimensioned depending on the items to be placed therein. In some embodiments, the width of each pocket 48 extends the entire width of the shoulder strap 26. The length of each pocket 48 may extend from the top of the shoulder strap 26 to the start of each adjustment strap 50. In some embodiments, each pocket 48 may have a length of about 3 inches to about 6 inches. In other embodiments, each pocket 48 may have a length of about 3.5 inches to about 5 inches. In still other embodiments, each pocket 48 may have a length of about 4 inches to about 4.5 inches. For example, the pockets 48 may have a length of about 4.5 inches.

In an exemplary embodiment, the shoulder straps 26 each include an adjustment strap 50 that allows the user to adjust the length and fit of the shoulder straps 26. The adjustment strap 50 is positioned on a surface of the shoulder strap 26 that faces away from the user so that the user may easily access the adjustment strap 50. The adjustment strap 50 extends from below the pockets 48 to the bottom of the shoulder strap 26. As illustrated in FIG. 3, the adjustment strap 50 is threaded through an upper buckle 52 and a lower buckle 54 positioned on the shoulder strap 26. The lower buckle 54 may be used to adjust the length of the adjustment strap 50. The shoulder straps 26 are tightened or cinched upon the shoulders by pulling on a free end 56 of each adjustment strap 50 that is threaded through the lower buckle 54. Conversely, the shoulder straps 26 are loosened by pulling upwardly on the lower buckle 54. This action allows slack to occur within the adjustment strap 50 so that the shoulder straps 26 may be loosened.

In some embodiments, the medical backpack 100 may also include a chest strap 58. The chest strap 58 is adjustably attached to the upper buckle 52 on each adjustment strap 50. The chest strap 58 includes a releasable fastening mechanism adjustably mounted thereon for fixedly securing the chest strap 58 around the user's chest. In one embodiment, the chest strap 58 includes a snap release buckle for fastening the chest strap 58 around the user's chest. The chest strap 58 may be adjusted to the center of the chest of the user to place the weight of backpack 100 to the center of the user's body.

In some embodiments, the medical backpack 100 may include a waistband 60. The waistband 60 includes two portions 62 attached to each lateral surface 20 that are connected together with an adjustable strap having a releasable buckle. The medical backpack 100 should generally be positioned on the user's back such that the adjustable strap of the waistband 60 wraps around the user's waist portion.

The waistband 60 helps to distribute the weight load of the medical backpack to the hips and waist of the user, relieving some shoulder pressure.

Figure 4:
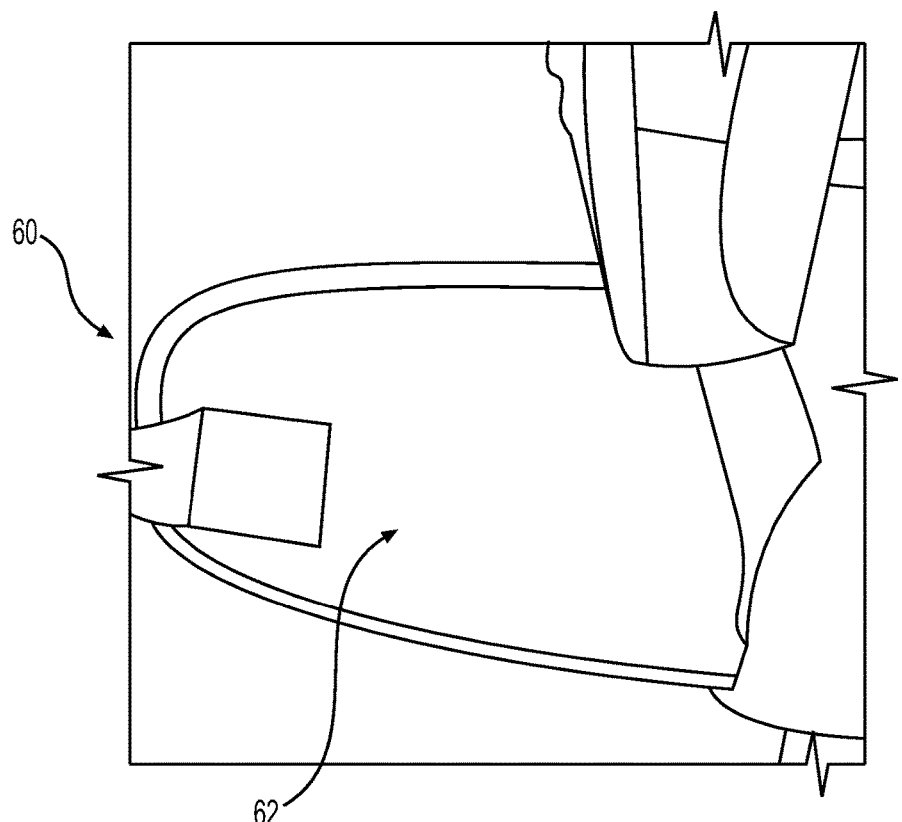
FIG. 4 is a side view of a waistband on the medical backpack according to one embodiment of the present disclosure.

FIG. 4 shows one of the portions 62 of the waistband 60. The portion 62 shown in FIG. 4 has a generally curved oval shape so that each portion 62 sits comfortably against the user's hips and waist. Each portion 62 may be sized and dimensioned depending on the size of the user. In some embodiments, each portion 62 may have a maximum length of about 8 inches to about 12 inches. In other embodiments, each portion 62 may have a maximum length of about 9 inches to about 11 inches. In still other embodiments, each portion 62 may have a maximum length of about 10 inches. Each portion 62 may have a height sufficient to cover and comfortably rest against the user's hip bone. For example, each portion 62 may have a maximum height of about 4.5 inches to about 8 inches. In other embodiments, each portion 62 may have a maximum height of about 5 inches to about 7.5 inches. In still other embodiments, each portion 62 may have a maximum height of about 6.5 inches.

Figure 5:
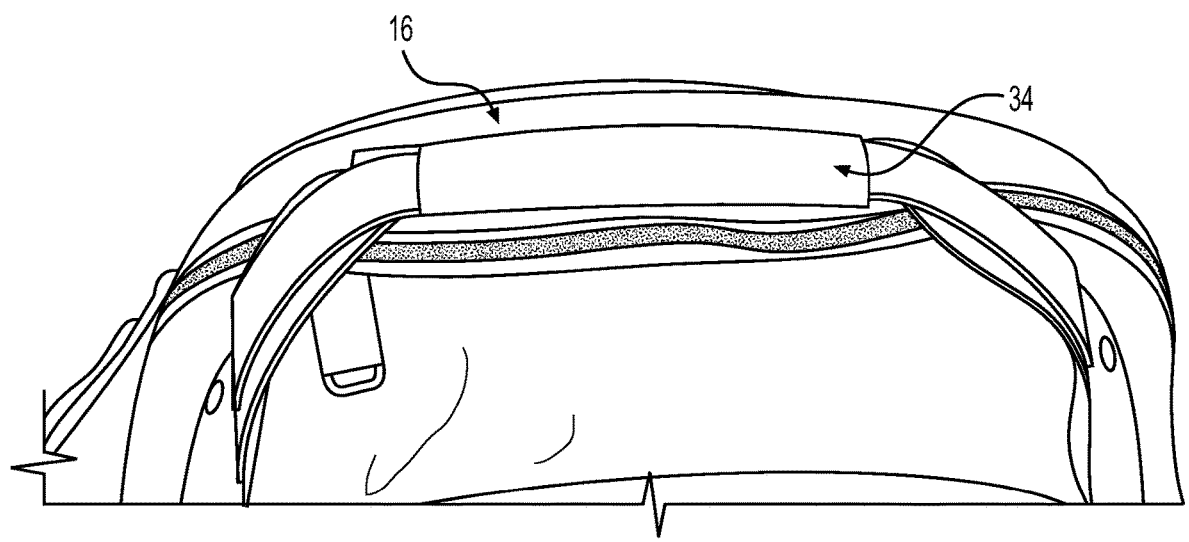
FIG. 5 is a perspective view of a handle on the medical backpack according to one embodiment of the present disclosure.

FIG. 5 shows the handle 34 affixed to the top surface 16 according to an exemplary embodiment of the present disclosure. The handle 34 may be malleable or it may be rigid. In some embodiments, the handle 34 may have a metal cover. For example, the handle 34 may be enclosed within a curved, tubular metal cover to protect the handle 34 from wear and tear. The curvature of the cover also improves the comfortability of the handle 34. The handle 34 may have enough rigidity to stand. In other embodiments, the handle 34 may sit flush with the top surface 16 and extend when pulled on by a user. The handle 34 may have any size that allows for a user to carry the medical backpack 100. In some embodiments, the handle 34 may have a length of about 3 inches to about 6 inches. In other embodiments, the handle 34 may have a length of about 3.5 inches to about 5 inches. For instance, the handle 34 may have a length of about 4.5 inches.

Figure 6A:
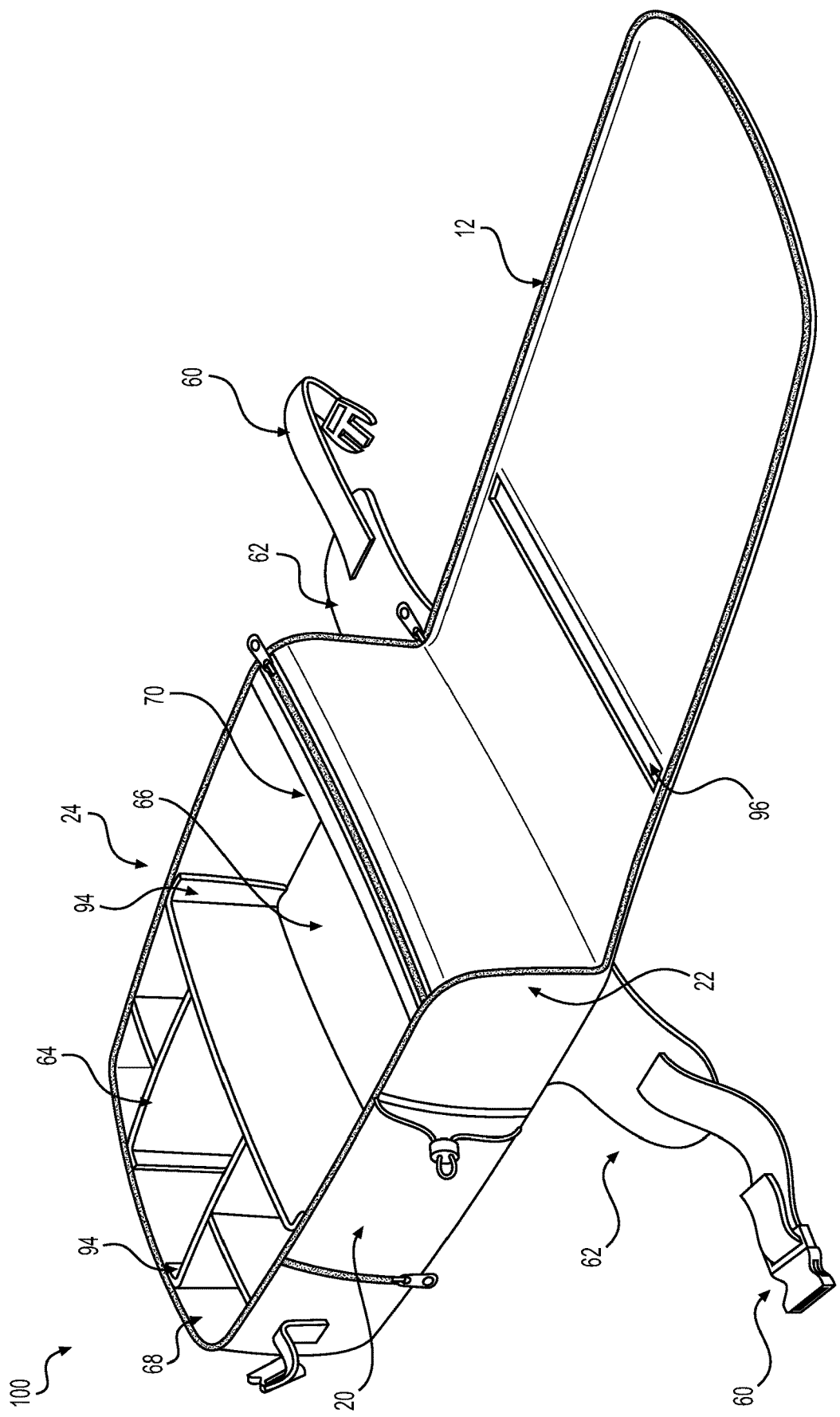
FIG. 6A is a perspective view of the interior of the medical backpack according to an exemplary embodiment of the present disclosure.

FIG. 6A shows the interior of the medical backpack 100 according to an exemplary embodiment. As shown in FIG. 6A, the main zipper 22 unzips to enable the front surface 12 to rotate outwardly with respect to the remaining portions of the backpack 100 and expose an interior cavity 24. The front surface 12 lies flat in the same plane as the rear surface 14. The interior cavity 24 includes a plurality of dividers 64. The dividers 64 attach along inner walls of the top surface 16 and the opposing lateral surfaces 20 to collectively form a plurality of compartments within the interior cavity 24. In some embodiments, the interior cavity 24 may include a plurality of dividers 64 that are positioned vertically and a plurality of dividers 64 that are positioned laterally. The dividers 64 may also have varying lengths depending on the desired size of the compartments.

In some embodiments, the dividers 64 may be removable so that the dividers 64 can be re-positioned within the interior cavity 24. For example, as shown in FIG. 6A, the dividers 64 may include a tab 94 having a hook and loop fastener attached thereto at each end that allows for the dividers 64 to be removably attached to the inner walls of the top surface 16 and the opposing lateral surfaces 20 and to other dividers 64 positioned within the interior cavity 24. In other embodiments, the dividers 64 may be removably attached within the interior cavity 24 using a plurality of slots or snap fasteners. In still other embodiments, the dividers 64 may be affixed within the interior cavity 24.

The dividers 64 are arranged within the interior cavity 24 to create a main compartment 66 and a plurality of ancillary compartments 68. In the illustrated embodiment, the dividers 64 are arranged to create five ancillary compartments 68. As will be described in more detail below, the main compartment 66 is designed to store a number of internal bags that each include a particular set of medical supplies arranged by type. The ancillary compartments 68 may be used to store various medical supplies that can fit in the smaller compartments. Each ancillary compartment 68 may be directed to storing a particular medical supply. For example, the ancillary compartments 68 may be used to store bandages, alcohol pads, thermometers, gloves, gauze pads, medical tape, medical scissors, small trash bags, Q-tips, tongue blades, saline, or other wound care supplies. In some embodiments, the ancillary compartments 68 may be used to store diagnostic tests, such as equipment for blood and/or urine testing. In further embodiments, each of the ancillary compartments 68 has a volume that is less than the volume of the main compartment 66. While the interior cavity 24 is illustrated as having one main compartment and five ancillary compartments, it will be apparent to those skilled in the art that any number of dividers 64 may be arranged in any fashion to create compartments of varying sizes and dimensions for particular medical or other supplies.

Figure 6B:
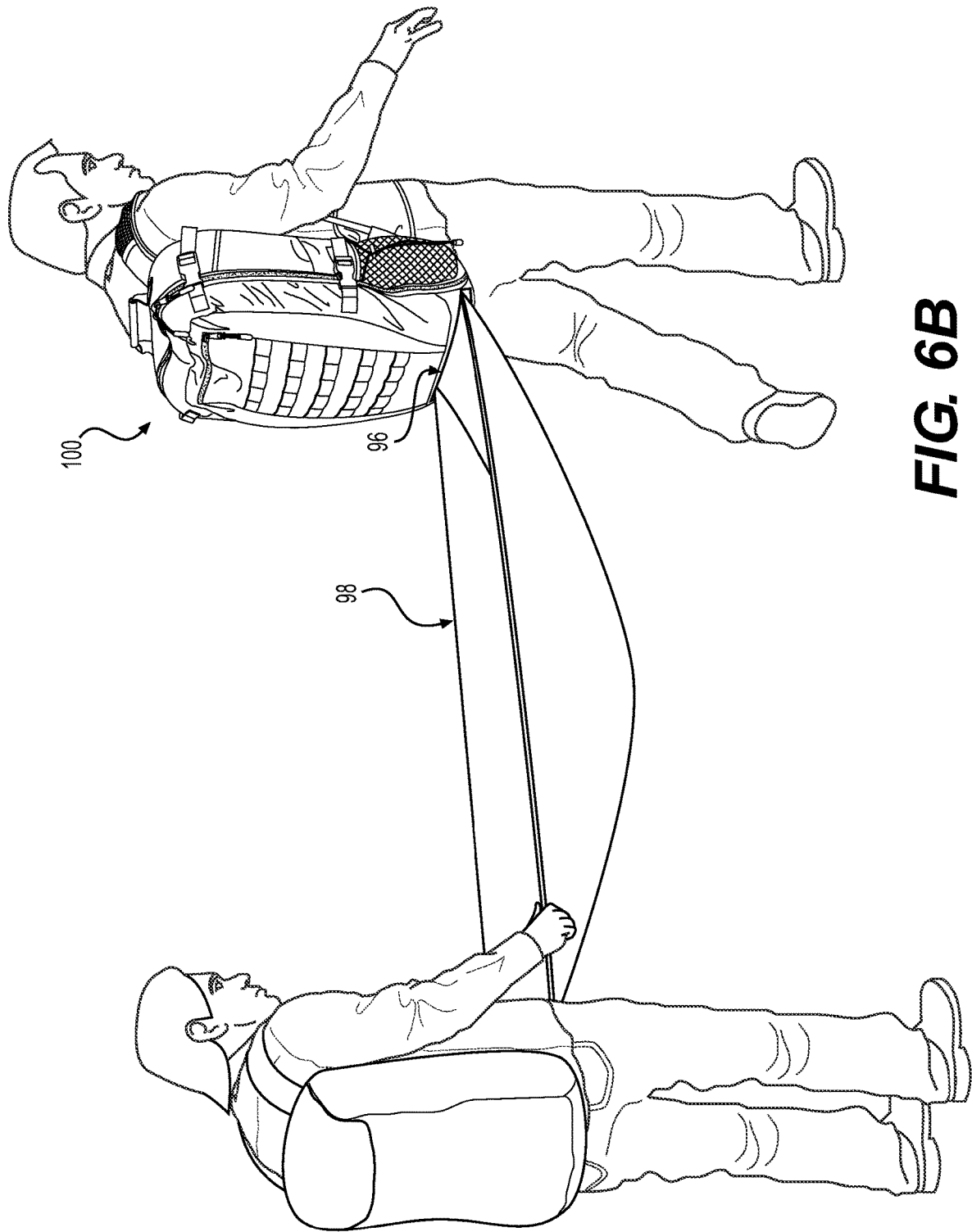
FIG. 6B is a perspective view of a portable stretcher attached to the medical backpack according to one embodiment of the present disclosure.

The interior cavity 24 may further include a zippered pocket 70 positioned adjacent to the bottom surface 18 and below the main compartment 66. The zippered pocket 70 may be used to store a portable stretcher. The portable stretcher may be a folding or flat stretcher that it is much lighter than a standard wheeled stretcher. In some embodiments, the front surface 12 may include a slot 96 in which the zippered pocket 70 may be accessed from the exterior of the medical backpack 100. As shown in FIG. 6B (described in more detail below), the pocket 70 may be unzipped by accessing the slot 96 and the portable stretcher may be pulled through the slot 96 and extended for use. In this embodiment, the portable stretcher may be accessed without unzippering the main zipper 22. In other embodiments, the zippered pocket 70 is only accessible when the main zipper 22 is unzipped. In still other embodiments, the zippered pocket 70 may be positioned on the exterior of the medical backpack 100. In still further embodiments, the zippered pocket 70 may further comprise a spool or reel to aid in pulling the portable stretcher in and out of the medical backpack 100.

FIG. 6B shows a portable stretcher 98 in use with the medical backpack 100. As shown in FIG. 6B, the pocket 70 may be unzipped from the exterior of the backpack 100 using the slot 96 and the portable stretcher 98 may be pulled through the slot 96 and extended for use. In this embodiment, one end of the portable stretcher 98 remains secured to the backpack body 10 while another user carries the opposing end of the portable stretcher 98. After use, the portable stretcher 98 may be folded or rolled up and inserted back into the pocket 70 for storage. For instance, the spool or reel in the zippered pocket 70 can aid in pulling the portable stretcher 98 back into the medical backpack 100.

Figure 7:
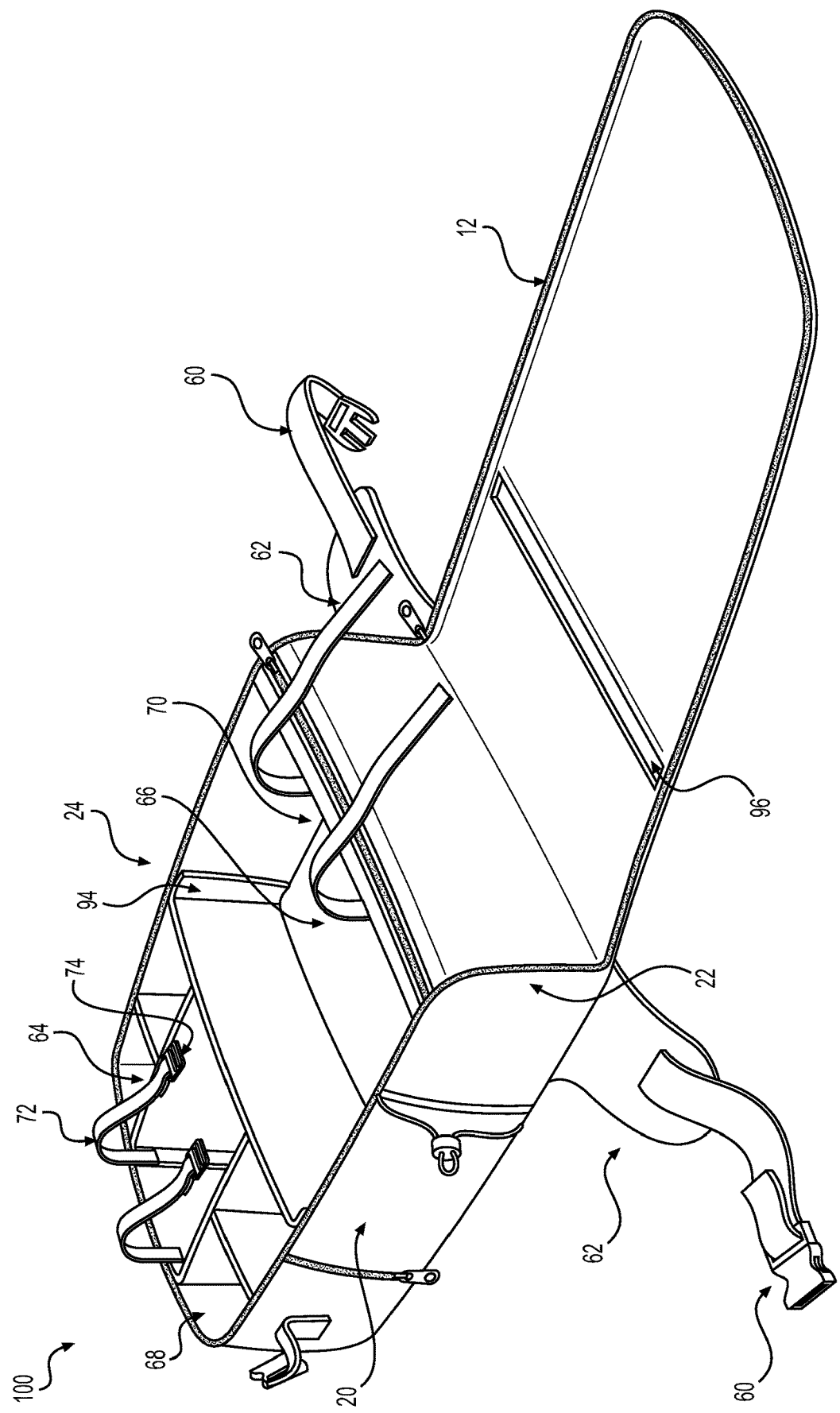
FIG. 7 is a perspective view of the interior of the medical backpack with securing straps according to one embodiment of the present disclosure.

FIG. 7 shows the interior of the medical backpack 100 with securing straps 72 attached therein. The interior cavity 24 may include one or more securing straps 72 for securing the internal bags and medical supplies stored within the main compartment 66 and the ancillary compartments 68. In the illustrated embodiment, the interior cavity 24 includes two securing straps 72 attached therein, with one end of each of the securing straps 72 attached to the top surface 16 and the other end of each of the securing straps 72 attached to the zippered pocket 70. In this embodiment, the securing straps 72 are positioned in a substantially vertical configuration. However, any number of securing straps 72 may be attached within the interior cavity 24 and may be positioned in other configurations, such as in horizontal or diagonal configurations.

The securing straps 72 each include a fastening clip 74, such as a D-ring fastening clip, through which one end of the securing strap 72 may pass. The fastening clip 74 allows for the securing straps 72 to be adjusted, for example, tightened or loosened, based on the amount of supplies stored in the main compartment 66 and the ancillary compartments 68. The securing straps 72 should have a length sufficient to extend along the length of the interior cavity 24. The width of the securing straps 72 may vary but should be sufficiently wide enough to secure the supplies within the interior cavity 24. In some embodiments, the securing straps 72 may have a width of about 0.5 inches to about 3 inches. In other embodiments, the securing straps 72 may have a width of about 1 inches to about 2 inches. For example, the securing straps 72 may have a width of about 1 inch.

Figure 8B:
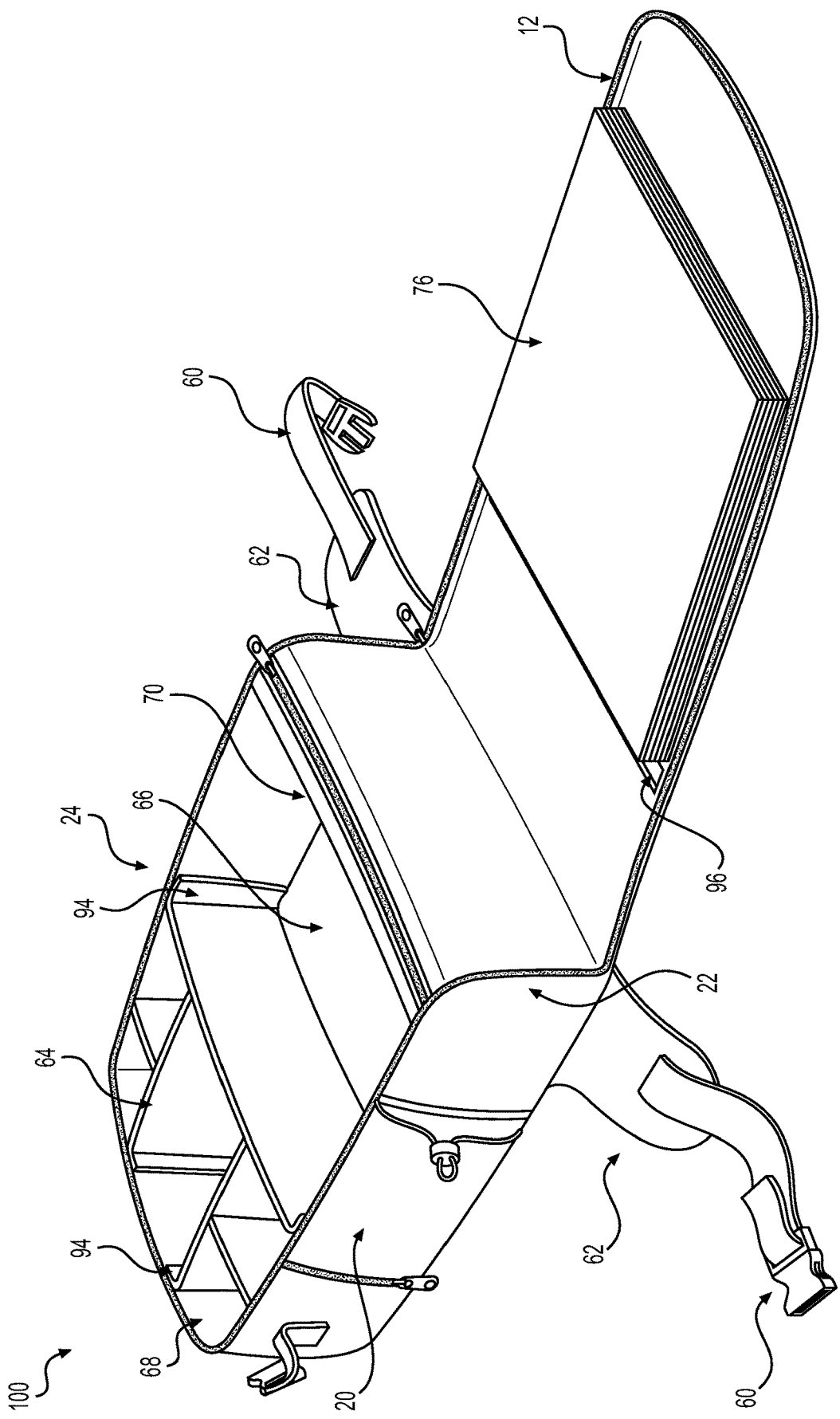
FIG. 8B is a perspective view of the interior of the medical backpack with a plurality of panels folded inwardly according to one embodiment of the present disclosure.

FIGS. 8A and 8B show the interior of the medical backpack 100 according to another embodiment of the present disclosure. In this embodiment, an inner portion of the front surface 12 may include one or more panels that are designed to fold out from the front surface 12 to provide a larger work area with improved sterility. The main zipper 22 is designed to allow the front surface 12 when fully opened to lay flat, in the same plane as the rear surface 14, when fully unzipped, which promotes the ability to fold out the one or more panels and create the sterile work surface. In some embodiments, the medical backpack 100 may also include sterilizing wipes to enable the user to sterilize the panels and the front surface 12 to provide a sterile working surface. As illustrated in FIG. 8A, the front surface 12 includes an anchoring panel 77 removably affixed thereto and five additional panels 76 that fold outwardly from the anchoring panel 77 and lay flat, creating a large, flat surface for the work area. In this embodiment, the front surface 12 has six total panels attached thereto. As shown in FIG. 8B, after use, the panels 76 can fold inwardly over the anchoring panel 77, creating a compact stack of panels that allows for the medical backpack 100 to be closed and zippered. In some embodiments, one or more of the anchoring panel 77 and the panels 76 are affixed to the inner portion of the front surface 12, for example, by stitching. In other embodiments, one or more of the anchoring panel 77 and the panels 76 may be removably attached to the inner portion of the front surface 12. For instance, one or more of the anchoring panel 77 and the panels 76 may be attached using snap fasteners, hook and loop fasteners, adhesives, zippers, or clips. In still other embodiments, the panels 76 may be affixed to or removably attached to the anchoring panel 77 and each other.

The anchoring panel 77 and the panels 76 may be formed of one or more layers of any suitable material that provides sufficient durability. Suitable materials include, but are not limited to, acrylonitrile butadiene styrene (ABS), acetal, acrylic, polyvinyl chloride (PVC), polyester, high-density polyethylene (HDPE), polystyrene, nylon, polycarbonate, polypropylene, and any combination of the foregoing. In some embodiments, the panels 76 may have one layer, for example, an inner layer, formed of ABS and another layer, for example, an outer layer, formed of polyester. The anchoring panel 77 and the panels 76 may also include an insert to provide additional rigidity. In further embodiments, the outer surfaces of the anchoring panel 77 and the panels 76 (i.e., the work area surface) are sterile surfaces. In this embodiment, the outer surfaces of the anchoring panel 77 and the panels 76 may include a layer or coating of an antimicrobial agent. Suitable antimicrobial agents include, but are not limited to, biquanide, isothiazolones, metals, alcohols, silver-loaded zeolites, phenol or phenol derivatives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan, ammoniums (for example, bacteriostatic quaternary ammonium compounds such as benzalkonium chloride, benzethonium chloride, cetyl pyridium chloride, lauryl pyridium chloride and methyl benzethonium chloride); zinc phenol sulfonate; zinc ricinoleate; triethyl citrate; chitosan or chitin derivatives and combinations thereof. While FIGS. 8A and 8B show the use of six panels, one of ordinary skill in the art will appreciate that any number of panels may be used to create a flat work area. In addition, FIGS. 8A and 8B show the slot 96, the anchoring panel 77, and the panels 76; however, a skilled artisan will recognize that the anchoring panel 77 and the panels 76 may be used on a medical backpack without the use of the slot 96.

Figure 9:
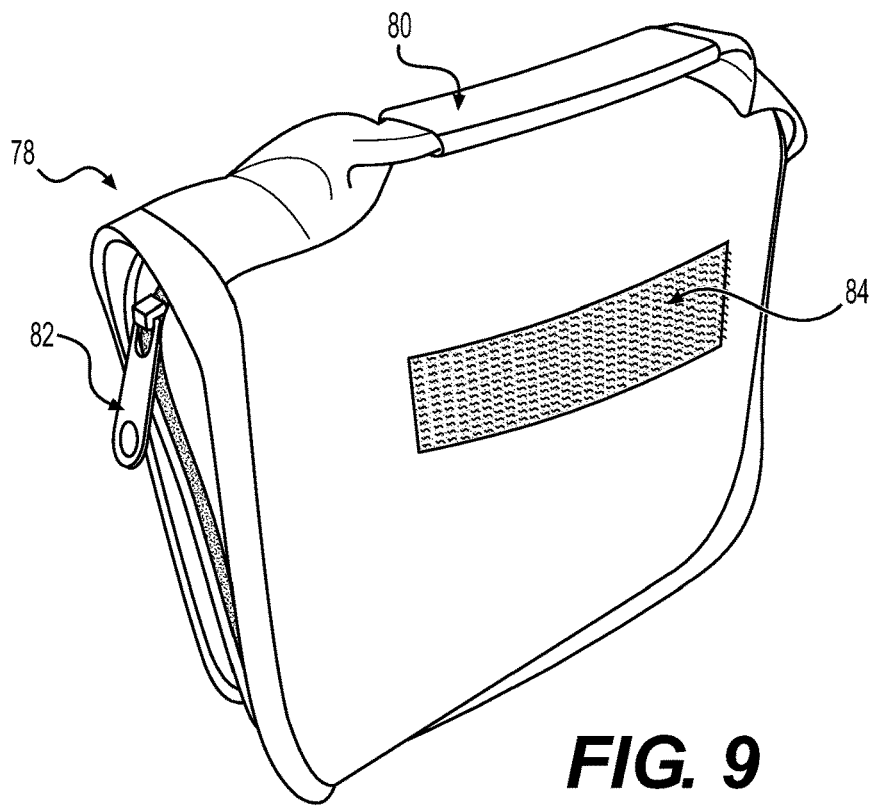
FIG. 9 is a perspective view of an internal bag for storing medical supplies and/or equipment according to one embodiment of the present disclosure.
Figure 16:
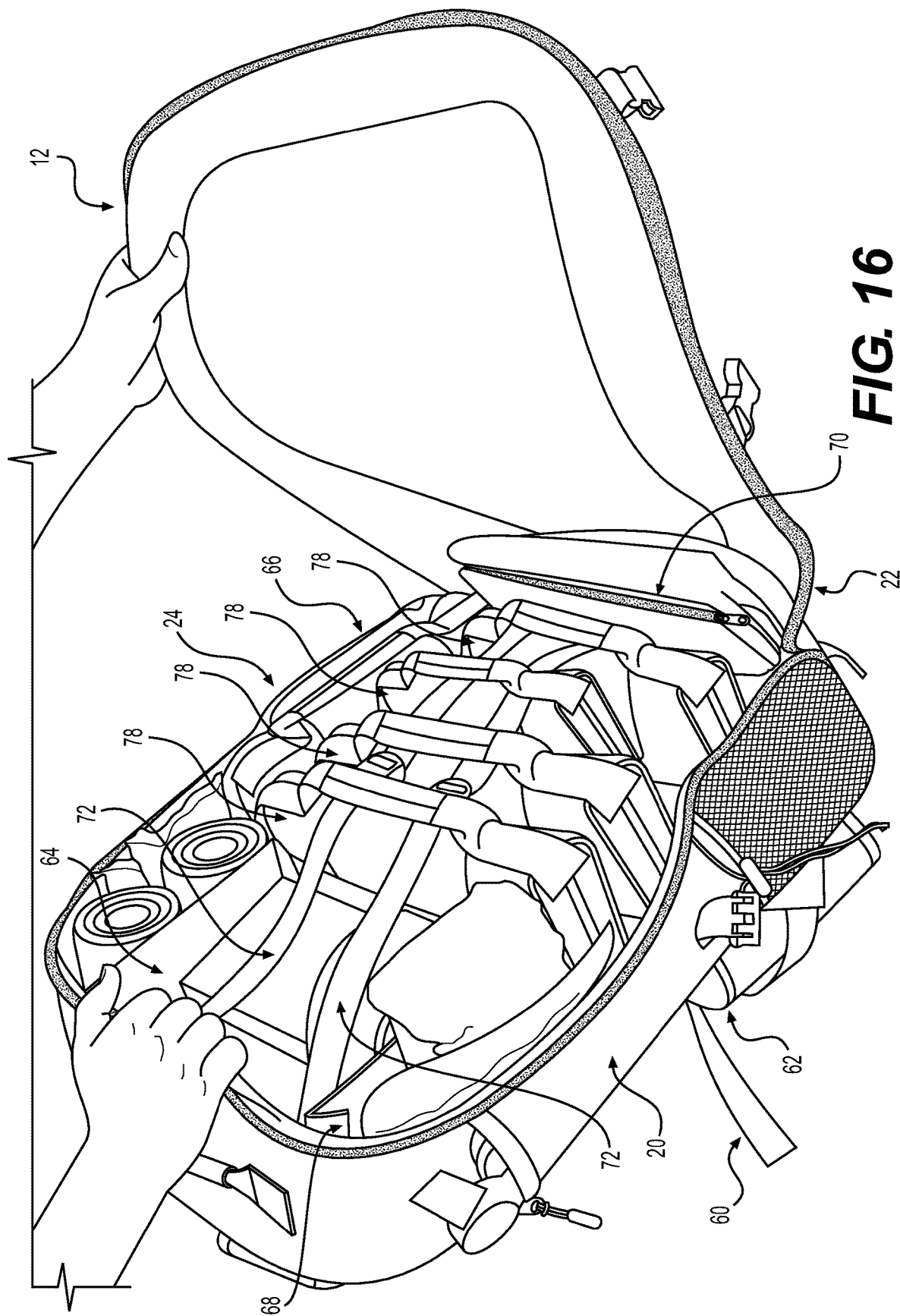
FIG. 16 is a perspective view of the interior of a medical backpack with internal bags secured therein according to one embodiment of the present disclosure.

FIG. 9 shows an internal bag 78 that may be placed within the interior cavity 24 according to one embodiment of the present disclosure. The internal bag 78 is designed to store medical supplies and equipment that may be needed by medics working in remote areas of the world. In some embodiments, a plurality of internal bags 78 may be stored in the main compartment 66. For example, as shown in FIG. 16 below, the internal bags 78 may be positioned alongside one another, forming a generally straight line. Each internal bag 78 is directed to storing a particular type of medical supply. For example, the medical backpack 100 may include an internal bag 78 for storing a suture kit that is composed of various instruments for stitching wounds, such as scalpels, probes, forceps, scissors, non-absorbable and absorbable sutures, hemostats, alcohol, and antibiotic cream. In other embodiments, the medical backpack 100 may include an internal bag 78 for storing a wound care kit that is composed of various supplies for cleaning, treating, and protecting cuts, scrapes, and burns. The wound care kit may include supplies, such as gauze pads, surgical pads, antiseptic wipes, non-stick pads, transparent dressings, rolled gauze, tape, and adhesive bandages. In still other embodiments, the medical backpack 100 may include an internal bag 78 for carrying various medicines, such as, for example, aloe vera gel, calamine lotion, anti-diarrhea medication, laxatives, antacids, antihistamines, such as diphenhydramine, hydrocortisone cream, cough and cold medications, epinephrine, and pain relievers, such as acetaminophen and ibuprofen. In yet other embodiments, the medical backpack 100 may include an internal bag 78 for storing various medical equipment and accessories, such as, for instance, diagnostic tests, supplies for providing intravenous (IV) medications, thermometers, flashlights, headlamps, gloves, and penlights with pupil gauges. In still further embodiments, the medical backpack 100 may include an internal bag 78 for storing a baby delivery kit. The baby delivery kit may include supplies such as, for instance, plastic liners, disposable gloves, gauze, razor blades and string, soap, baby blankets, and infant sleepers.

Each internal bag 78 includes a hook and loop fastener 84 attached thereto at the center of a front and/or back surface. The hook and loop fastener 84 allows for each internal bag 78 to be fastened to one another when the internal bags 78 are stored within the main compartment 66, which prevents the internal bags 78 from moving around when the medical backpack 100 is being carried. The hook and loop fasteners 84 should be sufficiently sized to allow for the internal bags 78 to be attached to one another. In some embodiments, the hook and loop fasteners 84 may be about 1 inch to about 3 inches in width, preferably about 1.5 inches, and about 4 inches to about 7 inches in length, preferably about 5 inches. Each internal bag 78 may also include a handle 80 positioned on a top surface. The handle 80 allows the user to carry each of the internal bags 78. The securing straps 72 discussed above can also be threaded through the handle 80 on each of the internal bags 78 when the internal bags 78 are stored within the main compartment 66 to prevent the bags 78 from moving around. Each internal bag 78 may be opened and closed using a zipper 82. As shown in FIG. 9, the zipper 82 extends along three of the four edges of the internal bag 78 to create a secure compartment and to enable the internal bag 78 to lay flat when opened.

Figure 10:
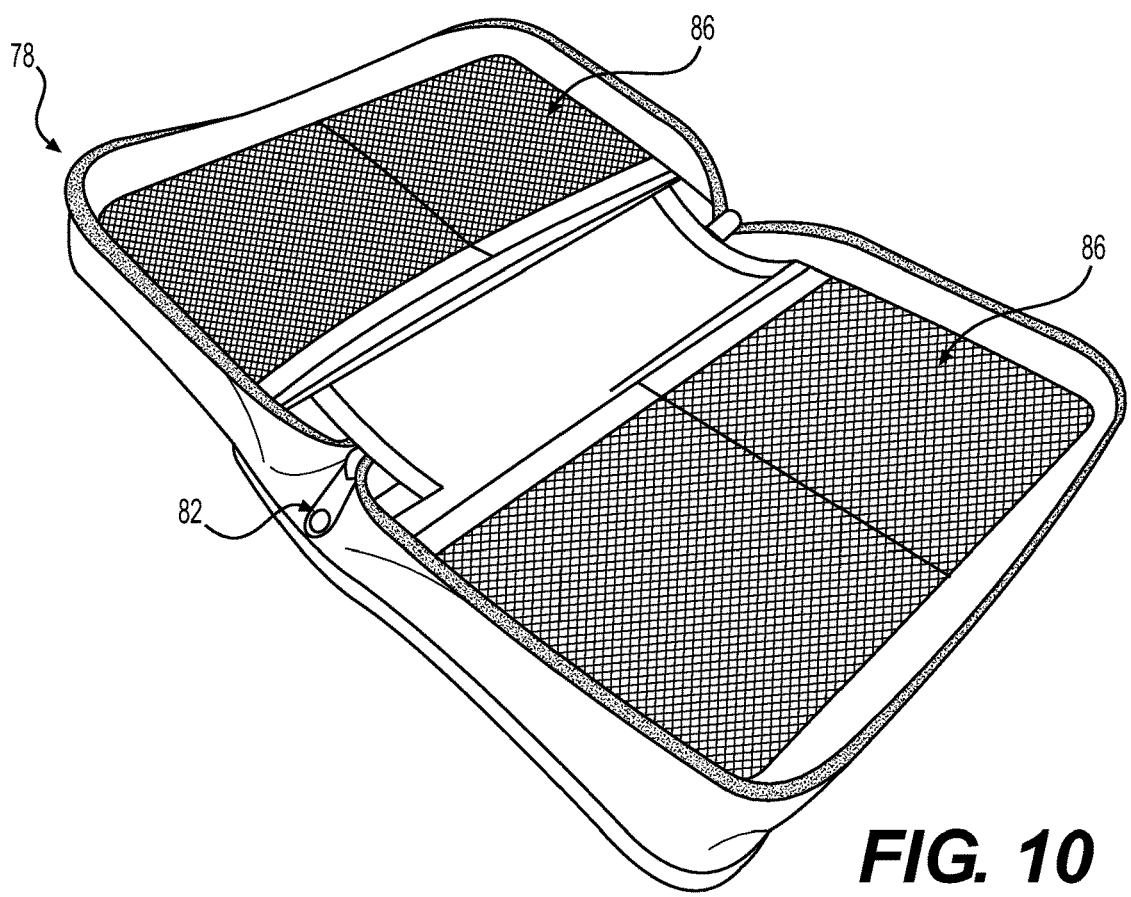
FIG. 10 is a perspective view of the interior of the internal bag of FIG. 9 according to one embodiment of the present disclosure.
Figure 11:
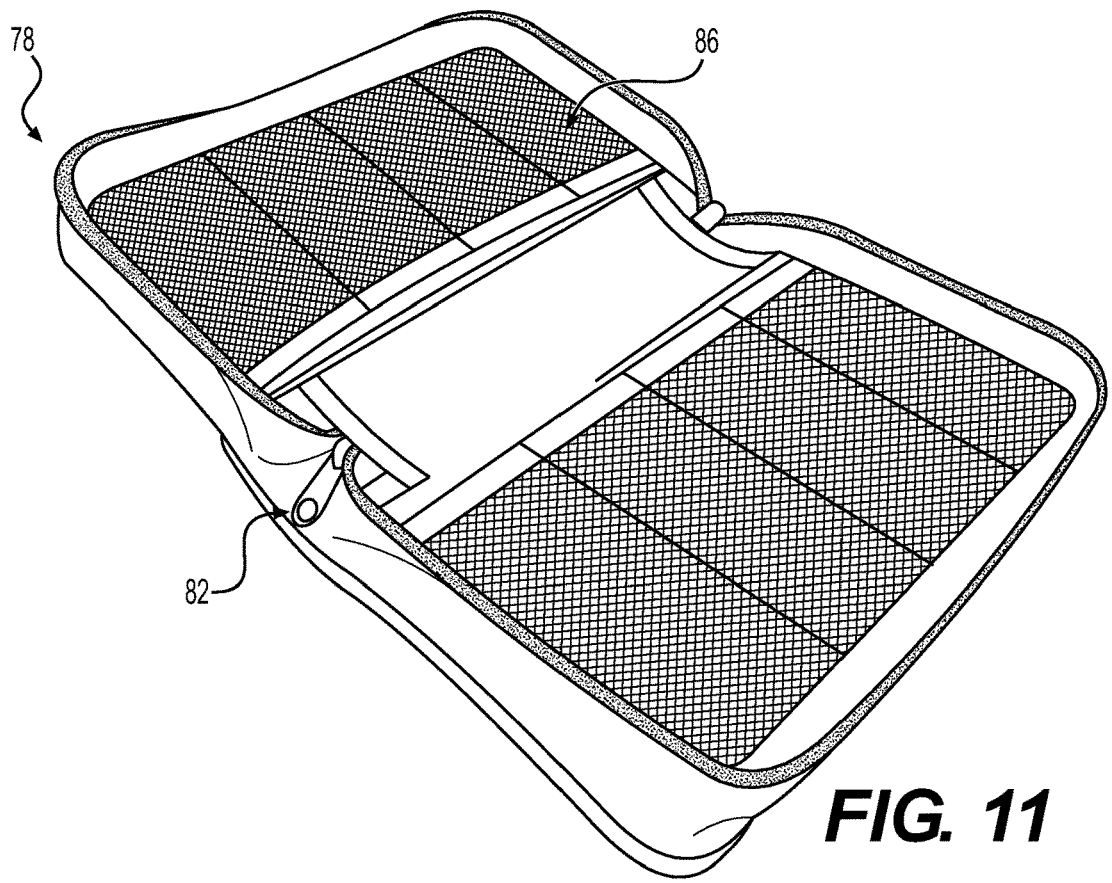
FIG. 11 is a perspective view of the interior of an internal bag according to another embodiment of the present disclosure.
Figure 12:
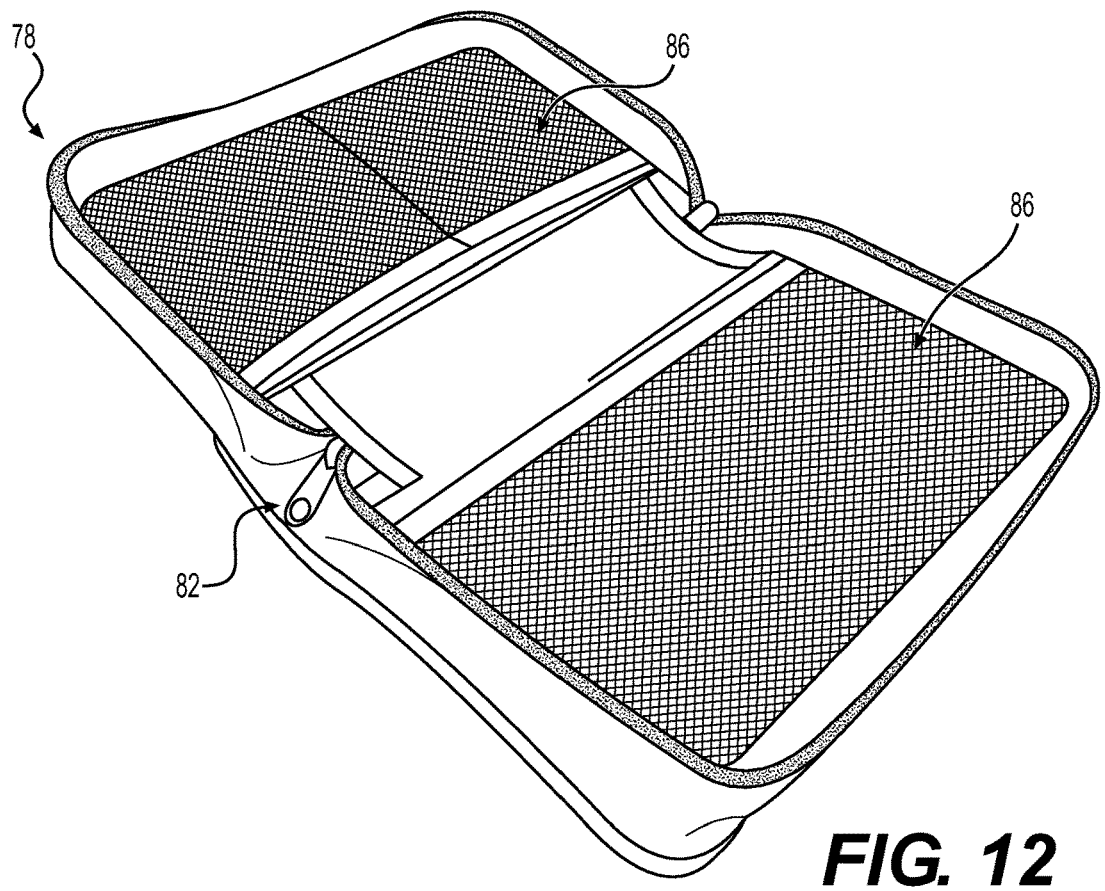
FIG. 12 is a perspective view of the interior of an internal bag according to still another embodiment of the present disclosure.

FIGS. 10, 11, and 12 show various configurations of internal pockets for use within the internal bag 78. The internal bag 78 may be unzipped along three of the four edges such that the internal bag 78 folds open to access pockets 86 within the interior of the internal bag 78. FIG. 10 illustrates the use of four pockets 86 within the internal bag 78. As shown in FIG. 10, there are two pockets on each side of the interior. FIG. 11 illustrates the use of eight pockets within the internal bag 78. As shown in FIG. 11, there are four pockets on each side of the interior. FIG. 12 illustrates the use of three pockets 86 within the internal bag 78. As shown in FIG. 12, there are two pockets on one side and a single large pocket on the opposing side of the interior. The number and size of the pockets 86 may vary depending on the type of supplies to be stored within the internal bag 78. For instance, the configuration shown in FIG. 11 may be desirable for storing smaller medical supplies, while the configuration shown in FIG. 12 may be desirable for storing larger medical instruments and equipment. The pockets 86 shown in FIGS. 10-12 are constructed of mesh. The mesh allows for the contents stored within the pockets 86 to be visible to the user so that the user can quickly access the correct supplies. However, the pockets 86 may be constructed of any other suitable material, such as plastic, fabric, or nylon.

Figure 13:
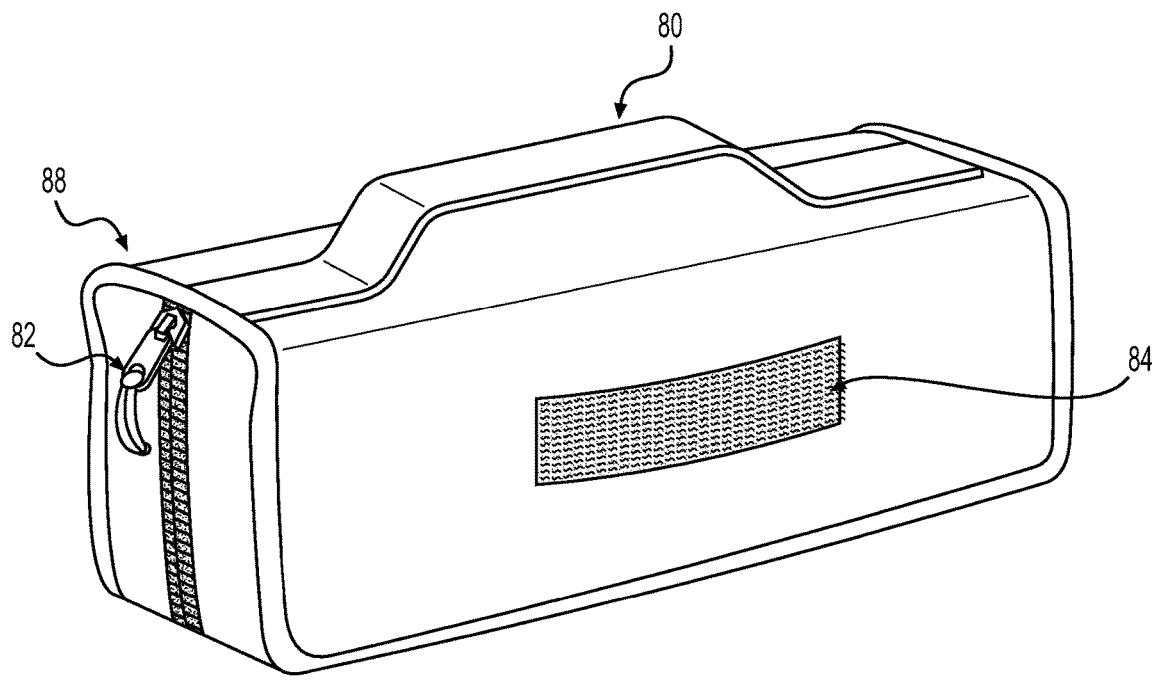
FIG. 13 is a perspective view of an elongated internal bag according to one embodiment of the present disclosure.

FIG. 13 shows an elongated internal bag 88 that may also be placed within the interior cavity 24. In one embodiment, the elongated internal bag 88 may be placed within the main compartment 66. The elongated internal bag 88 is designed to store larger medical equipment that may not fit within an internal bag 78 described above. For example, the medical backpack 100 may include an elongated internal bag 88 for storing a stethoscope and/or blood pressure equipment, such as blood pressure cuffs. In other embodiments, the medical backpack 100 may include an elongated internal bag 88 for storing an otoscope. The elongated internal bag 88 may be positioned lengthwise within the main compartment 66 such that the bag 88 is perpendicular to the internal bags 78. The elongated internal bag 88 may have a length that is longer than the length of the internal bag 78. In some embodiments, the elongated internal bag 88 has a length of about 10 inches to about 20 inches. In still other embodiments, the elongated internal bag 88 has a length of about 12 inches to about 18 inches. In yet other embodiments, the elongated internal bag 88 has a length of about 14 inches to about 16 inches. Similar to the internal bag 78 described above, the elongated internal bag 88 may include a hook and loop fastener 84 centered on a front and/or back surface and a handle 80 positioned on a top surface. The elongated internal bag 88 may also include a zipper 82 that extends along three of the four edges.

Figure 14:
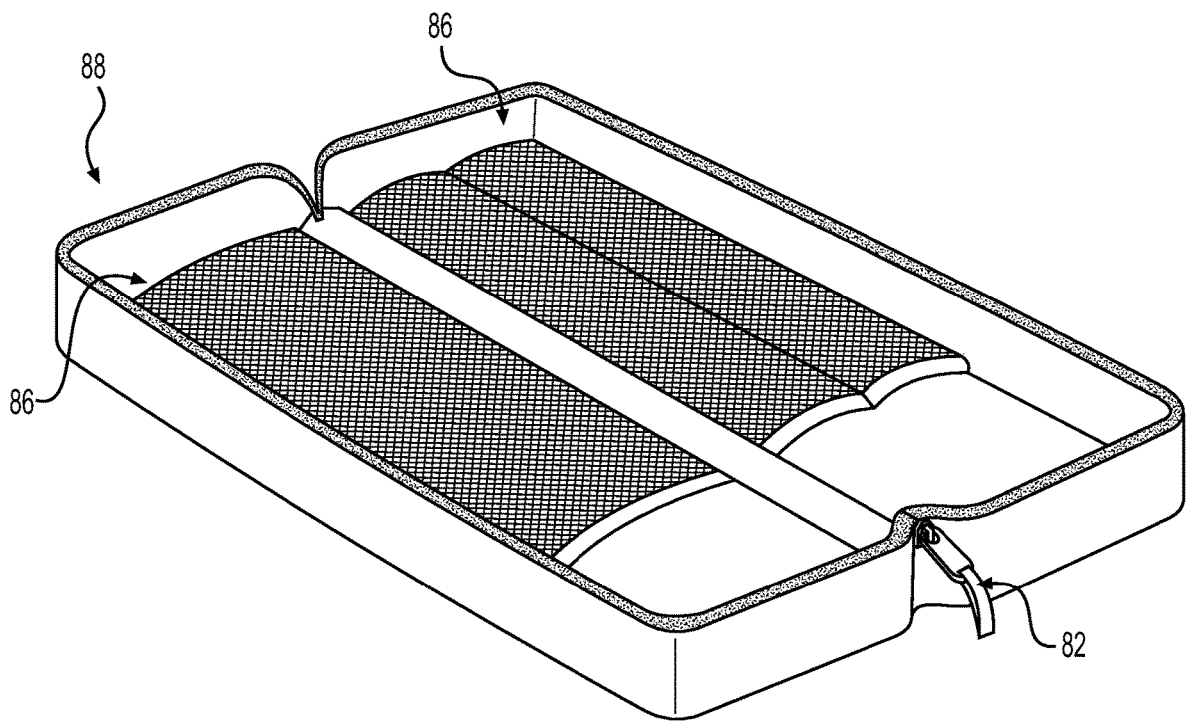
FIG. 14 is a perspective view of the interior of the elongated internal bag of FIG. 13 according to one embodiment.

FIG. 14 shows the pockets 86 within the elongated internal bag 88 according to one embodiment of the present disclosure. FIG. 14 illustrates the use of three pockets 86 within the elongated internal bag 88. As shown in FIG. 14, there are two pockets on one side and a single pocket on the opposing side of the interior. The length of the pockets 86 may vary depending on the type of medical equipment to be stored within the pockets 86. In some embodiments, the pockets 86 in the elongated internal bag 88 may have a length of about 5 inches to about 16 inches. In other embodiments, the pockets 86 in the elongated internal bag 88 may have a length of about 7 inches to about 13 inches. In still other embodiments, the pockets 86 in the elongated internal bag 88 may have a length of about 8 inches to about 10 inches. For instance, the pockets 86 in the elongated internal bag 88 may have a length of about 8 inches. The pockets 86 shown in FIG. 14 are constructed of mesh; however, the pockets 86 may be constructed of any other suitable material, such as plastic, fabric, or nylon.

Figure 15A:
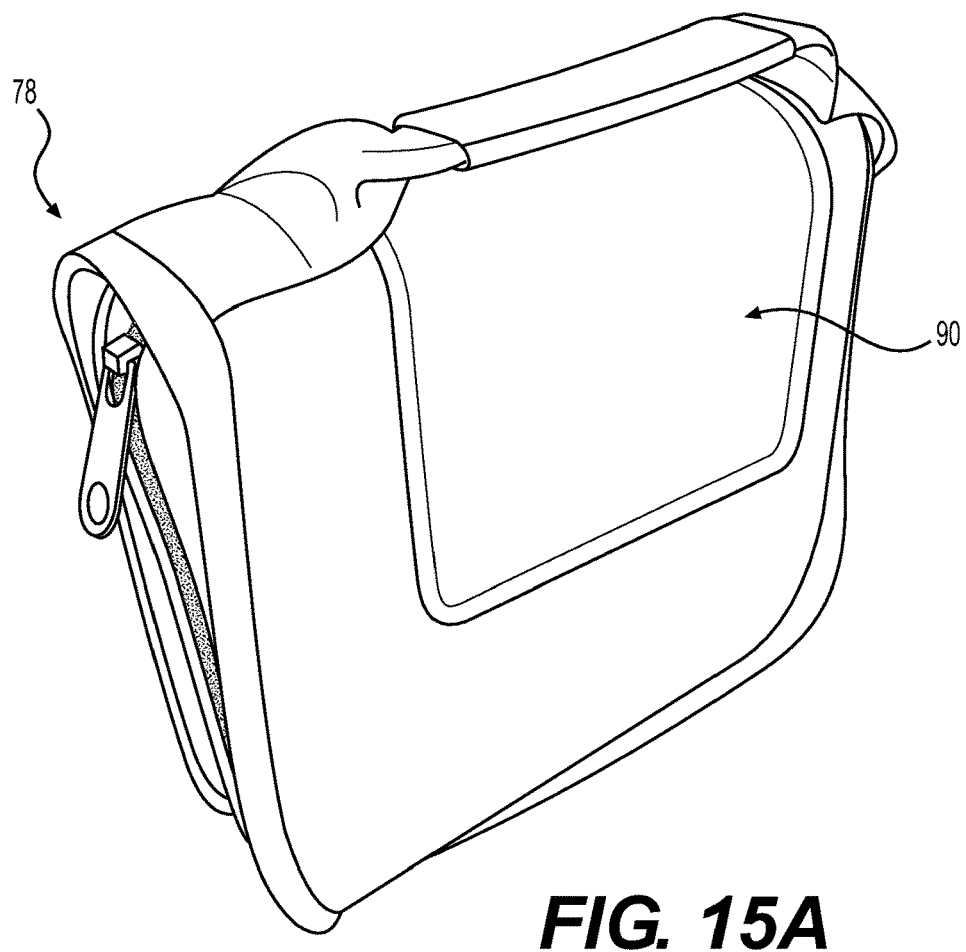
FIG. 15A is a perspective view of an internal bag having a label affixed thereto according to one embodiment of the present disclosure.
Figure 15B:
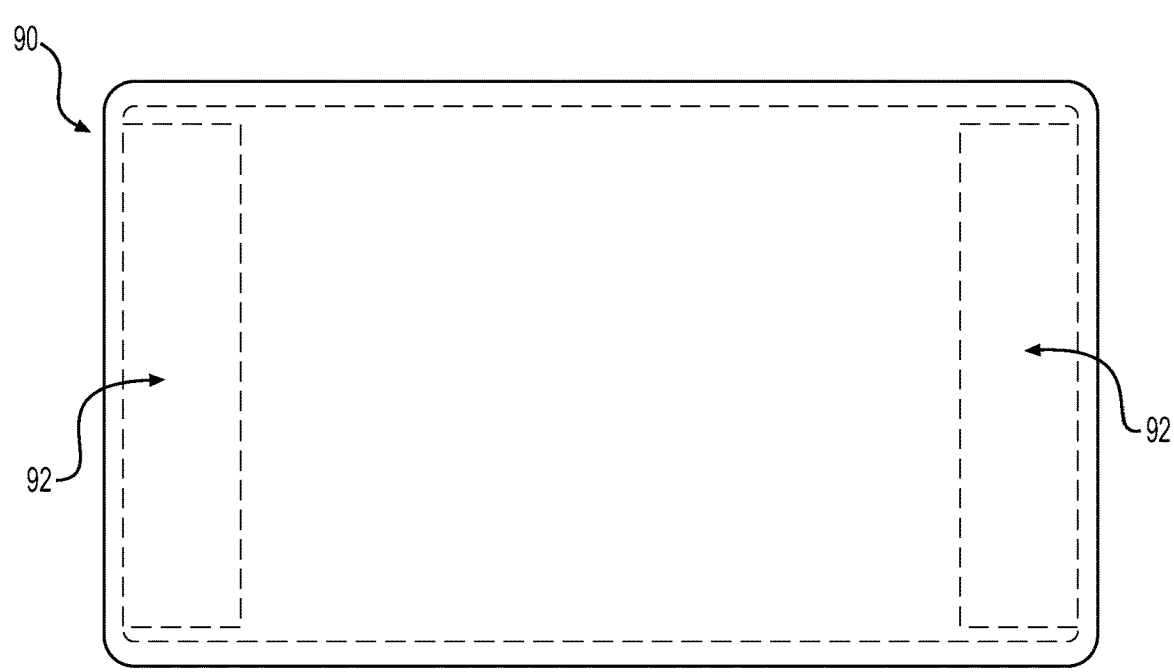
FIG. 15B is a front view of a label according to one embodiment of the present disclosure.

FIGS. 15A and 15B show a label 90 that may be used with the internal bags 78 and the elongated internal bags 88 described herein. As illustrated in FIG. 15A, the label 90 may be affixed to an outer surface of the internal bag 78 or the elongated internal bag 88. The label 90 provides a place to identify the contents stored within the internal bag 78 or the elongated internal bag 88. In some embodiments, the label 90 may be removably attached to the outer surface of the internal bag 78 or the elongated internal bag 88 using hook and loop fasteners, snaps, clips, or magnets. In this embodiment, the label 90 can be removed when the contents of the internal bag 78 or the elongated internal bag 88 are changed or replaced. In other embodiments, the label 90 may be permanently affixed to the outer surface of the internal bag 78 or the elongated internal bag 88 using stitching or an adhesive, such as glue. In this embodiment, the label 90 may be a dry erase label that allows the user to erase and re-write the contents if the contents are replaced.

FIG. 15B shows an exemplary label 90 according to the present disclosure. As illustrated in FIG. 15B, the label 90 may include two hook and loop fasteners 92 positioned on each side of the label 90. The hook and loop fasteners 92 can be placed on the underside of the label 90 so that the hook and loop fasteners 92 may be secured to corresponding hook and loop fasteners 92 on the outer surface of the internal bag 78 or the elongated internal bag 88. The label 90 may be made of fabric, plastic, or any other material that is durable and will not easily tear. As shown in FIG. 15B, the label 90 may be affixed to the internal bag 78 or the elongated internal bag 88 using stitching, which is represented by the dashed line along the border of the label 90. In some embodiments, the labels 90 affixed to the internal bags 78 and the elongated internal bags 88 may be color coded such that the labels 90 have visually perceptible characteristics corresponding to the supplies stored therein. In other embodiments, the internal bags 78 and the elongated internal bags 88 themselves may be color coded based on the supplies stored therein.

FIG. 16 shows an interior view of the medical backpack 100 with a plurality of internal bags 78 positioned therein. As shown in FIG. 16, four internal bags 78 are positioned within the main compartment 66 in a generally straight line such that the hook and loop fasteners 84 on each bag 78 can be fastened to one another. The securing straps 72 can be threaded through the handles 80 of each of the bags 78 to secure the internal bags 78 in place. As further illustrated in FIG. 16, the ancillary compartments 68 may be used to store various other medical supplies. However, it is to be understood that a user could utilize a variety of combinations of internal bags, elongated internal bags, and dividers to arrange the interior cavity to store a variety of combinations of medical supplies for different applications.

The backpacks described and claimed herein are not to be limited in scope by the specific embodiments herein disclosed, since these embodiments are intended as illustrations of several aspects of the disclosure. Any equivalent embodiments are intended to be within the scope of this disclosure. Indeed, various modifications of the backpacks in addition to those shown and described herein will become apparent to those skilled in the art from the foregoing description. Such modifications are also intended to fall within the scope of the disclosure. All patents and patent applications cited in the foregoing text are expressly incorporated herein by reference in their entirety. Any section headings herein are provided only for consistency with the suggestions of 37 C.F.R. § 1.77 or otherwise to provide organizational queues. These headings shall not limit or characterize the invention(s) set forth herein.

What is claimed is:

1. A medical backpack, comprising:
    a backpack body defining an interior cavity, the backpack body defined by a front surface having four edges, a rear surface, a top surface, a bottom surface, and opposing lateral surfaces,
    a zipper fastener extending along three of the four edges defining the front surface, wherein the zipper fastener unzips to enable the front surface to rotate outwardly with respect to the remaining portions of the backpack body, and thereby enabling access to the interior cavity,
    at least one shoulder strap coupled to the backpack body,
    a plurality of dividers arranged within the interior cavity to form a main compartment and a plurality of ancillary compartments, wherein the main compartment is configured for receiving a plurality of internal bags, wherein each internal bag comprises a handle,
    a portable stretcher having a proximal end and a distal end,
    a pocket within the interior cavity, wherein the proximal end of the portable stretcher is attached to the pocket,
    wherein the front surface comprises a slot in alignment with the pocket and the portable stretcher is configured to extend through the slot such that the distal end of the portable stretcher may be positioned external to the interior cavity with the proximal end remaining attached to the pocket, and
    wherein the main compartment comprises a securing strap attached thereto and the securing strap is configured to be threaded through the handle of each internal bag received within the main compartment to secure the internal bags.

2. The medical backpack of claim 1, wherein the backpack body comprises a plurality of attachment points configured for attaching hooks or carabiners thereto.

3. The medical backpack of claim 1, further comprising a handle enclosed within a curved, tubular metal cover.

4. The medical backpack of claim 1, further comprising a zippered pocket positioned above the expandable mesh pocket on the backpack body.

5. The medical backpack of claim 1, wherein each of the ancillary compartments has a volume that is less than the volume of the main compartment.

6. The medical backpack of claim 1, wherein the portable stretcher is adapted for carrying an individual.

7. A medical backpack, comprising:
- a backpack body defining an interior cavity, the backpack body defined by a front surface having four edges, a rear surface, a top surface, a bottom surface, and opposing lateral surfaces,
- a zipper fastener extending along three of the four edges defining the front surface, wherein the zipper fastener unzips to enable the front surface to rotate outwardly with respect to the remaining portions of the backpack body so that the front surface lies substantially coplanar with the rear surface,
- a plurality of dividers arranged within the interior cavity to form a main compartment and a plurality of ancillary compartments,
- a plurality of internal bags received within the main compartment, each internal bag comprising a handle,
- a portable stretcher having a proximal end and a distal end,
- a pocket within the interior cavity configured for storing the portable stretcher, wherein the proximal end of the portable stretcher is attached to the pocket,
- wherein the front surface comprises a slot in alignment with the pocket and the portable stretcher is configured to extend through the slot such that the distal end of the portable stretcher may be positioned external to the interior cavity with the proximal end remaining attached to the pocket, and
- wherein the main compartment comprises a plurality of securing straps attached thereto and the securing straps are configured to be threaded through the handle of each internal bag to secure the internal bags within the main compartment.

8. The medical backpack of claim 7, wherein the plurality of internal bags comprises a first internal bag having a first length and a second internal bag having a second length, wherein the second length is longer than the first length.

9. The medical backpack of claim 7, wherein each of the internal bags comprises a fastener configured for directly attaching the internal bags to one another.

10. The medical backpack of claim 7, wherein each internal bag is directed to a specific medical supply or device and comprises a label affixed thereto identifying the specific medical supply or device stored therein.

11. A medical backpack, comprising:
- a backpack body defining an interior cavity, the backpack body further comprising a front surface having four edges,
- a zipper fastener extending along three of the four edges defining the front surface, wherein the zipper fastener unzips to enable the front surface to rotate outwardly with respect to the remaining portions of the backpack body, and thereby enabling access to the interior cavity,
- a plurality of dividers arranged within the interior cavity to form a main compartment and a plurality of ancillary compartments,
- a plurality of internal bags received within the main compartment, each internal bag comprising a handle and a fastener, wherein the fastener is configured for attaching the internal bags to one another, and wherein the main compartment comprises a securing strap attached thereto, the securing strap configured to be threaded through the handle of each internal bag to secure the internal bags within the main compartment,
- a portable stretcher having a proximal end and a distal end,
- a pocket within the interior cavity configured for storing the portable stretcher, wherein the proximal end is attached to the pocket, and
- the front surface further comprising a slot in alignment with the pocket, wherein the portable stretcher is configured to extend through the slot such that the distal end of the portable stretcher may be positioned external to the interior cavity with the proximal end remaining attached to the pocket.

12. The medical backpack of claim 11, further comprising a strapping system comprising two shoulder straps coupled to the backpack body, a chest strap coupled to the two shoulder straps, and an adjustable waistband coupled to the backpack body.

13. The medical backpack of claim 11, wherein the plurality of internal bags comprises a first internal bag configured for storing a suture kit, a second internal bag configured for storing a wound care kit, a third internal bag configured for storing medication, a fourth internal bag configured for storing a baby delivery kit, a fifth internal bag configured for storing a stethoscope, blood pressure equipment, or a combination thereof, and a sixth internal bag configured for storing an otoscope.

14. The medical backpack of claim 11, wherein each of the internal bags comprises a label removably attached thereto identifying a medical supply or device stored therein.

* * * * *